United States Patent
Anderson et al.

(10) Patent No.: US 7,842,686 B2
(45) Date of Patent: Nov. 30, 2010

(54) CGRP RECEPTOR ANTAGONISTS

(75) Inventors: Corey Don Anderson, San Diego, CA (US); Andreas P. Termin, San Diego, CA (US); Pramod Joshi, San Diego, CA (US); Sara S. Hadida Ruah, La Jolla, CA (US); Daniele Bergeron, La Mesa, CA (US); Sanghee Yoo, San Diego, CA (US); Jingrong Cao, Newton, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 12/356,745

(22) Filed: Jan. 21, 2009

(65) Prior Publication Data

US 2009/0186882 A1    Jul. 23, 2009

Related U.S. Application Data

(63) Continuation of application No. PCT/US2007/016559, filed on Jul. 23, 2007.

(60) Provisional application No. 60/832,397, filed on Jul. 21, 2006.

(51) Int. Cl.
*C07D 413/12* (2006.01)
*C07D 417/12* (2006.01)
*A61K 31/536* (2006.01)
*A61K 31/5415* (2006.01)
*A61P 25/06* (2006.01)

(52) U.S. Cl. .................... 514/211.04; 514/211.06; 514/211.07; 514/221; 514/224.5; 514/230.5; 514/249; 540/491; 540/517; 544/52; 544/70; 544/105; 544/353

(58) Field of Classification Search ............ 514/211.04, 514/211.06, 211.07, 221, 224.5, 230.5, 249; 540/491, 517; 544/52, 70, 105, 353
See application file for complete search history.

(56) References Cited

FOREIGN PATENT DOCUMENTS

| WO | 2004/082605 | 9/2004 |
|---|---|---|
| WO | 2004/087649 | 10/2004 |

OTHER PUBLICATIONS

The International Search Report received in the corresponding PCT Application No. PCT/US2007/016559.

*Primary Examiner*—Bruck Kifle
(74) *Attorney, Agent, or Firm*—Michael C. Badia

(57) ABSTRACT

The present invention relates to CGRP receptor antagonists, pharmaceutical compositions thereof, and methods therewith for treating CGRP receptor-mediated diseases and conditions.

23 Claims, No Drawings

CGRP RECEPTOR ANTAGONISTS

CROSS REFERENCE TO RELATED APPLICATIONS

This application is a continuation of co-pending International Application number PCT/US2007/016559, filed Jul. 23, 2007, titled "CGRP RECEPTOR ANTAGONISTS", which claims the benefit under 35 U.S.C. § 119(e) of U.S. provisional application Ser. No. 60/832,397, titled "CGRP RECEPTOR ANTAGONISTS", filed Jul. 21, 2006, the entire contents of each application being incorporated herein by reference.

TECHNICAL FIELD OF THE INVENTION

The present invention relates to CGRP receptor antagonists, pharmaceutical compositions thereof, and methods therewith for treating CGRP receptor-mediated diseases and conditions.

BACKGROUND OF THE INVENTION

CGRP (Calcitonin Gene-Related Peptide) is a naturally occurring 37-amino acid peptide that is generated by tissue-specific alternate processing of calcitonin messenger RNA and is widely distributed in the central and peripheral nervous system. CGRP is localized predominantly in sensory afferent and central neurons and mediates several biological actions, including vasodilation. CGRP is expressed in alpha- and beta-forms that vary by one and three amino acids in the rat and human, respectively. CGRP-alpha and CGRP-beta display similar biological properties. When released from the cell, CGRP initiates its biological responses by binding to specific cell surface receptors that are predominantly coupled to the activation of adenylyl cyclase. CGRP receptors have been identified and pharmacologically evaluated in several tissues and cells, including those of brain, cardiovascular, endothelial, and smooth muscle origin.

CGRP is a potent vasodilator that has been implicated in the pathology of cerebrovascular disorders such as migraine and cluster headache. In clinical studies, elevated levels of CGRP in the jugular vein were found to occur during migraine attacks (Goadsby et al., Ann. Neurol., 1990, 28, 183-187). CGRP activates receptors on the smooth muscle of intracranial vessels, leading to increased vasodilation, which is thought to be the major source of headache pain during migraine attacks (Lance, Headache Pathogenesis: Monoamines, Neuropeptides, Purines and Nitric Oxide, Lippincott-Raven Publishers, 1997, 3-9). The middle meningeal artery, the principle artery in the dura mater, is innervated by sensory fibers from the trigeminal ganglion which contain several neuropeptides, including CGRP. Trigeminal ganglion stimulation in the cat resulted in increased levels of CGRP, and in humans, activation of the trigeminal system caused facial flushing and increased levels of CGRP in the external jugular vein (Goadsby et al., Ann. Neurol., 1988, 23, 193-196). Electrical stimulation of the dura mater in rats increased the diameter of the middle meningeal artery, an effect that was blocked by prior administration of CGRP(8-37), a peptide CGRP antagonist (Williamson et al., Cephalalgia, 1997, 17, 525-531). Trigeminal ganglion stimulation increased facial blood flow in the rat, which was inhibited by CGRP(8-37) (Escott et al., Brain Res. 1995, 669, 93-99). Electrical stimulation of the trigeminal ganglion in marmoset produced an increase in facial blood flow that could be blocked by the non-peptide CGRP antagonist BIBN4096BS (Doods et al., Br. J. Pharmacol., 2000, 129, 420-423). Thus the vascular effects of CGRP may be attenuated, prevented or reversed by a CGRP antagonist. In recently reported clinical trials, the CGRP receptor antagonist BIBN 4096 BS was reported to be effective in treating acute attacks of migraine (Olesen et al., N. Engl. J. Med. 2004, 350:1104-1110).

CGRP-mediated vasodilation of rat middle meningeal artery was shown to sensitize neurons of the trigeminal nucleus caudalis (Williamson et al., The CGRP Family: Calcitonin Gene-Related Peptide (CGRP), Amylin, and Adrenomedullin, Landes Bioscience, 2000, 245-247). Similarly, distention of dural blood vessels during migraine headache may sensitize trigeminal neurons. Some of the associated symptoms of migraine, including extra-cranial pain and facial allodynia, may be the result of sensitized trigeminal neurons (Burstein et al., Ann. Neurol. 2000, 47, 614-624). A CGRP antagonist may be beneficial in attenuating, preventing or reversing the effects of neuronal sensitization.

The ability of the compounds of the present invention to act as CGRP antagonists makes them useful pharmacological agents for disorders that involve CGRP in humans and animals, but particularly in humans. Such disorders include migraine and cluster headache (Doods, Curr Opin Inves Drugs, 2001, 2 (9), 1261-1268; Edvinsson et al., Cephalalgia, 1994, 14, 320-327); chronic tension type headache (Ashina et al., Neurology, 2000, 14, 1335-1340); pain (Yu et al., Eur. J. Pharm., 1998, 347, 275-282); chronic pain (Hulsebosch et al., Pain, 2000, 86, 163-175); neurogenic inflammation and inflammatory pain (Holzer, Neurosci., 1988, 24, 739-768; Delay-Goyet et al., Acta Physiol. Scanda. 1992, 146, 537-538; Salmon et al., Nature Neurosci., 2001, 4(4), 357-358); eye pain (May et al. Cephalalgia, 2002, 22, 195-196), tooth pain (Awawdeh et al., Int. Endocrin. J., 2002, 35, 30-36), non-insulin dependent diabetes mellitus (Molina et al., Diabetes, 1990, 39, 260-265); vascular disorders; inflammation (Zhang et al., Pain, 2001, 89, 265), arthritis, bronchial hyperreactivity, asthma, (Foster et al., Ann. NY Acad. Sci., 1992, 657, 397-404; Schini et al., Am. J. Physiol., 1994, 267, H2483-H2490; Zheng et al., J. Virol., 1993, 67, 5786-5791); shock, sepsis (Beer et al., Crit. Care Med., 2002, 30 (8), 1794-1798); opiate withdrawal syndrome (Salmon et al., Nature Neurosci., 2001, 4(4), 357-358) morphine tolerance (Menard et al., J. Neurosci., 1996, 16 (7), 2342-2351); hot flashes in men and women (Chen et al., Lancet, 1993, 342, 49; Spetz et al., J. Urology, 2001, 166, 1720-1723); allergic dermatitis (Wallengren, Contact Dermatitis, 2000, 43 (3), 137-143); psoriasis; encephalitis, brain trauma, ischaemia, stroke, epilepsy, and neurodegenerative diseases (Rohrenbeck et al., Neurobiol. of Disease 1999, 6, 15-34); skin diseases (Geppetti and Holzer, Eds., Neurogenic Inflammation, 1996, CRC Press, Boca Raton, Fla.), neurogenic cutaneous redness, skin rosaceousness and erythema; tinnitus (Herzog et al., J. Membrane Biology, 2002, 189(3), 225); inflammatory bowel disease, irritable bowel syndrome, (Hoffman et al. Scandinavian Journal of Gastroenterology, 2002, 37(4) 414-422) and cystitis. Of particular importance is the acute or prophylactic treatment of headache, including migraine and cluster headache.

The present invention relates to compounds that are useful as ligands for CGRP receptors, in particular antagonists of CGRP receptors, pharmaceutical compositions thereof, and uses therewith.

SUMMARY OF THE INVENTION

The present invention provides compounds of formula (I):

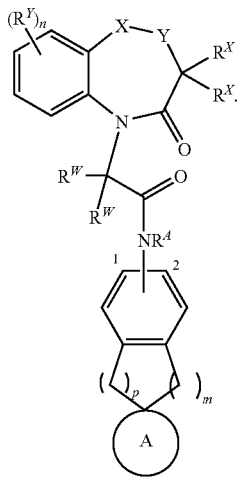

(I)

These compounds are useful as antagonists of CGRP receptors and thus treating CGRP-mediated conditions. The present invention also provides pharmaceutical compositions thereof and uses therewith.

DETAILED DESCRIPTION OF THE INVENTION

The present invention provides compounds of formula I:

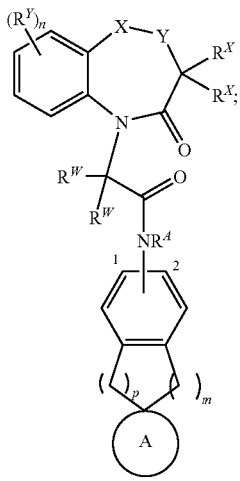

(I)

or a pharmaceutically acceptable salt thereof;

wherein:

said $NR^A$ group is attached to the phenyl ring at carbon atom 1 or 2;

X is O, $NR^A$, S, SO, or $SO_2$;

$R^A$ is hydrogen or C1-C6 aliphatic optionally substituted with up to 4 $R^1$ substituents;

ring A is a 4-7 membered heterocyclic ring having 1-4 heteroatoms selected from O, N, S, SO, or $S(O)_2$, wherein said heterocyclic ring is optionally fused to a phenyl or a 5-7 membered heterocyclic or heteroaryl ring having 1-4 heteroatoms selected from O, N, S, SO, or $S(O)_2$; wherein ring A has at least one oxo substituent;

wherein ring A, together with the optionally fused ring, is optionally substituted with up to 5 $R^2$ substituents;

m is 1-3;

p is 1-3;

n is 1-4;

Y is a bond, $C(R^X)_2$, or $-C(R^X)_2-C(R^X)_2-$;

or wherein $-X-Y-$ is $-C(R^X)_2-C(R^X)_2-$, $-C(R^X)_2-C(R^X)_2-C(R^X)_2-$, $-C(R^X)_2-NR^A-$ or $-C(R^X)_2-C(R^X)_2-NR^A-$;

each $R^X$ is independently hydrogen, halo, aryl, heteroaryl, C1-C6 aliphatic, C1-C6 heteroaliphatic, aryl-C1-C6 aliphatic, aryl-C1-C6 heteroaliphatic, heteroaryl-C1-C6 aliphatic, heteroaryl-C1-C6 heteroaliphatic, or $Q-R^M$, wherein $R^X$ is optionally substituted with up to 5 $R^3$ substituents; or two $R^X$, taken together with the carbon atom that they are attached to, form a 3-9 membered cycloaliphatic or heterocyclic ring, wherein said heterocyclic ring has up to 3 heteroatoms selected from O, S, and N; wherein said ring is optionally substituted with up to 3 $R^3$ substituents;

each $R^W$ is independently hydrogen, halo, aryl, heteroaryl, C1-C6 aliphatic, C1-C6 heteroaliphatic, aryl-C1-C6 aliphatic, heteroaryl-C1-C6 aliphatic, wherein $R^W$ is optionally substituted with up to 5 $R^4$ substituents; or two $R^W$, taken together with the carbon atom that they are attached to, form a 3-9 membered cycloaliphatic or heterocyclic ring, wherein said heterocyclic ring has up to 3 heteroatoms selected from O, S, and N; wherein said ring is optionally substituted with up to 3 $R^4$ substituents;

wherein each occurrence of $R^1$, $R^2$, $R^3$, $R^4$, and $R^Y$ is independently $Q-R^M$;

wherein Q is a bond or is a $C_1-C_6$ aliphatic chain wherein up to two non-adjacent methylene units of Q are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR;

wherein each occurrence of $R^M$ is independently selected from R', halogen, $NO_2$, CN, OR', SR', N(R')$_2$, NR'C(O)R', NR'C(O)N(R')$_2$, $NR'CO_2R'$, C(O)R', $CO_2R'$, OC(O)R', C(O)N(R')$_2$, OC(O)N(R')$_2$, SOR', $SO_2R'$, $SO_2N(R')_2$, $NR'SO_2R'$, $NR'SO_2N(R')_2$, C(O)C(O)R', or C(O)CH$_2$C(O)R';

wherein each occurrence of R is independently selected from hydrogen or an optionally substituted C1-C6 aliphatic group or C1-C6 heteroaliphatic; and wherein each occurrence of R' is independently selected from hydrogen or an optionally substituted group selected from $C_{1-8}$ aliphatic, $C_{6-10}$ aryl, a heteroaryl ring having 5-10 ring atoms, or a heterocyclyl ring having 3-10 ring atoms, or wherein R and R' taken together with the atom(s) to which they are bound, or two occurrences of R' taken together with the atom(s) to which they are bound, form a 3-8 membered cycloalkyl, heterocyclyl, aryl, or heteroaryl ring having 0-3 heteroatoms independently selected from nitrogen, oxygen, or sulfur.

Compounds of this invention include those described generally above, and are further illustrated by the classes, subclasses, and species disclosed herein. As used herein, the following definitions shall apply unless otherwise indicated.

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic or tricyclic $C_8$-$C_{14}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl. Suitable cycloaliphatic groups include cycloalkyl, bicyclic cycloalkyl (e.g., decalin), bridged bicycloalkyl such as norbornyl or [2.2.2]bicyclo-octyl, or bridged tricyclic such as adamantyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched.

The term "heterocycle", "heterocyclyl", "heterocycloaliphatic", or "heterocyclic" as used herein means non-aromatic, monocyclic, bicyclic, or tricyclic ring systems in which one or more ring atom is an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, or nitrogen (including, any oxidized forms thereof, e.g., S=O, $SO_2$, etc.; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The terms "haloaliphatic" and "haloalkoxy" means aliphatic or alkoxy, as the case may be, substituted with one or more halo atoms. The term "halogen" or "halo" means F, Cl, Br, or I. Examples of haloaliphatic include —$CHF_2$, —$CH_2F$, —$CF_3$, —$CF_2$—, or perhaloalkyl, such as, —$CF_2CF_3$.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from halo; —$R^o$; —$OR^o$; —$SR^o$; 1,2-methylene-dioxy; 1,2-ethylenedioxy; phenyl (Ph) optionally substituted with $R^o$; —O(Ph) optionally substituted with $R^o$; —$(CH_2)_{1-2}$(Ph), optionally substituted with $R^o$; —CH=CH(Ph), optionally substituted with $R^o$; —$NO_2$; —CN; —$N(R^o)_2$; —$NR^oC(O)R^o$; —$NR^oC(O)N(R^o)_2$; —$NR^oCO_2R^o$; —$NR^oNR^oC(O)R^o$; —$NR^oNR^oC(O)N(R^o)_2$; —$NR^oNR^oCO_2R^o$; —C(O)C(O)$R^o$; —C(O)$CH_2$C(O)$R^o$; —$CO_2R^o$; —C(O)$R^o$; —C(O)N($R^o)_2$; —OC(O)N($R^o)_2$; —$S(O)_2R^o$; —$SO_2N(R^o)_2$; —S(O)$R^o$; —$NR^oSO_2N(R^o)_2$; —$NR^oSO_2R^o$; —C(=S)N($R^o)_2$; —C(=NH)—N($R^o)_2$; or —$(CH_2)_{0-2}$NHC(O)$R^o$ wherein each independent occurrence of $R^o$ is selected from hydrogen, optionally substituted $C_{1-6}$ aliphatic, an unsubstituted 5-6 membered heteroaryl or heterocyclic ring, phenyl, —O(Ph), or —$CH_2$(Ph), or, notwithstanding the definition above, two independent occurrences of $R^o$, on the same substituent or different substituents, taken together with the atom(s) to which each $R^o$ group is bound, form a 3-8-membered cycloalkyl, heterocyclyl, aryl, or heteroaryl ring having 0-3 heteroatoms independently selected from nitrogen, oxygen, or sulfur. Optional substituents on the aliphatic group of $R^o$ are selected from $NH_2$, NH($C_{1-4}$aliphatic), N($C_{1-4}$aliphatic)$_2$, halo, $C_{1-4}$aliphatic, OH, O($C_{1-4}$aliphatic), $NO_2$, CN, $CO_2H$, $CO_2(C_{1-4}$aliphatic), O(halo$C_{1-4}$ aliphatic), or halo$C_{1-4}$aliphatic, wherein each of the foregoing $C_{1-4}$aliphatic groups of $R^o$ is unsubstituted.

An aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted C$_{1-6}$ aliphatic. Optional substituents on the aliphatic group of R* are selected from NH$_2$, NH(C$_{1-4}$ aliphatic), N(C$_{1-4}$ aliphatic)$_2$, halo, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$ aliphatic groups of R* is unsubstituted.

Optional substituents on the nitrogen of a non-aromatic heterocyclic ring are selected from —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, or —NR$^+$SO$_2$R$^+$; wherein R$^+$ is hydrogen, an optionally substituted C$_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of R$^+$, on the same substituent or different substituents, taken together with the atom(s) to which each R$^+$ group is bound, form a 3-8-membered cycloalkyl, heterocyclyl, aryl, or heteroaryl ring having 0-3 heteroatoms independently selected from nitrogen, oxygen, or sulfur. Optional substituents on the aliphatic group or the phenyl ring of R$^+$ are selcted from NH$_2$, NH(C$_{1-4}$ aliphatic), N(C$_{1-4}$ aliphatic)$_2$, halo, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$ aliphatic groups of R$^+$ is unsubstituted.

The term "spirocyclic ring system" refers to a moiety comprising two or more rings, wherein at least one ring has two points of attachment to another ring through a common carbon ring atom.

As detailed above, in some embodiments, two independent occurrences of R$^o$ (or R$^+$, or any other variable similarly defined herein), are taken together together with the atom(s) to which each variable is bound to form a 3-8-membered cycloalkyl, heterocyclyl, aryl, or heteroaryl ring having 0-3 heteroatoms independently selected from nitrogen, oxygen, or sulfur. Exemplary rings that are formed when two independent occurrences of R$^o$ (or R$^+$, or any other variable similarly defined herein) are taken together with the atom(s) to which each variable is bound include, but are not limited to the following: a) two independent occurrences of R$^o$ (or R$^+$, or any other variable similarly defined herein) that are bound to the same atom and are taken together with that atom to form a ring, for example, N(R$^o$)$_2$, where both occurrences of R$^o$ are taken together with the nitrogen atom to form a piperidin-1-yl, piperazin-1-yl, or morpholin-4-yl group; and b) two independent occurrences of R$^o$ (or R$^+$, or any other variable similarly defined herein) that are bound to different atoms and are taken together with both of those atoms to form a ring, for example where a phenyl group is substituted with two occurrences of OR$^o$

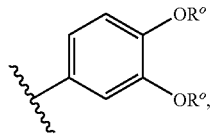

these two occurrences of R$^o$ are taken together with the oxygen atoms to which they are bound to form a fused 6-membered oxygen containing ring:

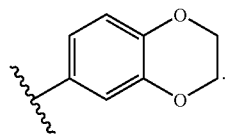

It will be appreciated that a variety of other rings can be formed when two independent occurrences of R$^o$ (or R$^+$, or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

In one embodiment, m is 1 and p is 1. In another embodiment, m is 1 and p is 2. Or, m is 2 and p is 1. Or, m is 2 and p is 2.

In one embodiment, X is O, NR$^A$, S, SO, or SO$_2$ and Y is a bond, C(R$^X$)$_2$, or —C(R$^X$)$_2$—C(R$^X$)$_2$—.

In one embodiment, X is O or S.

In one embodiment, Y is a bond.

In another embodiment, Y is C(R$^X$)$_2$. In another embodiment, Y is —CH$_2$

In yet another embodiment, Y is —C(R$^X$)$_2$—C(R$^X$)$_2$—. Or, Y is —CH$_2$—CH$_2$—.

In one embodiment, each R$^X$ is hydrogen.

In one embodiment, at least one R$^X$ is C1-C6 aliphatic optionally substituted with one or more halo, OH, C1-C4 alkoxy, C1-C4 alkoxy carbonyl, or di-(C1-C4 alkyl)amino. Exemplary embodiments include methyl, ethyl, propyl, isopropyl, butyl, t-butyl, 3,3-dimethyl-butyl, 3-methyl-butyl, 2-methyl-propyl, 2-methoxy-ethyl, 3-ethoxypropyl, 1-(methoxy carbonyl)-3-methyl-butyl, 1-(hydroxy methyl)-3-methyl-butyl, allyl, acetenyl, 2-(diethylamino)ethyl, 1-methyl-2-methoxy-ethyl, 3-hydroxy-2,2-dimethyl-propyl, 2,2, 2-trifluoroethyl, 3,3,3-trifluoro-propyl, or 2,2,3,3,3-pentafluoro-propyl. In a further embodiment, the one or more other $R^X$ is hydrogen.

In another embodiment, at least one $R^X$ is phenyl or heteroaryl optionally substituted with one or more substituents independently selected from C1-C6 aliphatic, cyano, halo, halo-C1-C6 aliphatic, aryl-C1-C6 aliphatic, heteroaryl-C1-C6 aliphatic, aralkyloxy, di (C1-C6 aliphatic)amino, O—C1-C6 aliphatic, S(O)—C1-C6 aliphatic, or S(O)$_2$—C1-C6 aliphatic. In a further embodiment, the one or more other $R^X$ is hydrogen.

In another embodiment, at least one $R^X$ is an optionally substituted C3-C7 cycloaliphatic or a heterocycloaliphatic ring having up to three heteroatoms selected from O, N, or S, wherein said ring is optionally fused to one or more phenyl or heteroaryl ring. Exemplary rings include cyclopentyl, cyclohexyl, cyclohexenyl, cycloheptyl, tetrahydro-2H-pyranyl, tetrahydro-2H-thiopyranyl, 9H-fluoren-9-yl or piperidinyl. In a further embodiment, the one or more other $R^X$ is hydrogen.

In another embodiment, two $R^X$, taken together with the carbon atom that they are attached to, form an optionally substituted 3-9 membered cycloaliphatic or heterocyclic, monocyclic, bicyclic, or tricyclic ring. Exemplary embodiments include 9H-fluoroen-9-yl, tetrahydro-2H-pyran-4-yl, tetrahydro-2H-thiopyran-4-yl, cyclopropyl, cyclobutyl, cyclopentyl, cyclohexyl, cycloheptyl, cyclohexenyl, piperidinyl, or 1-benzyl-piperidin-4-yl.

In another embodiment, at least one $R^X$ is —C(O)NH—$R^M$, —OC(O)—$R^M$, —NHC(O)—$R^M$, NHC(O)O—$R^M$, wherein $R^M$ is an optionally substituted phenyl, heteroaryl or heterocyclic group. In a further embodiment, the one or more other $R^X$ is hydrogen.

In one embodiment, both $R^W$ are hydrogen.

In one embodiment, one $R^W$ is hydrogen and the other $R^W$ is C1-C6 aliphatic optionally substituted with one or more halo, OH, C1-C4 alkoxy, C1-C4 alkoxy carbonyl, or di-(C1-C4 alkyl)amino. Exemplary embodiments include methyl, ethyl, propyl, isopropyl, butyl, t-butyl, 3,3-dimethyl-butyl, 3-methyl-butyl, 2-methyl-propyl, 2-methoxy-ethyl, 3-ethoxypropyl, 1-(methoxy carbonyl)-3-methyl-butyl, 1-(hydroxy methyl)-3-methyl-butyl, allyl, acetenyl, 2-(diethylamino) ethyl, 1-methyl-2-methoxy-ethyl, 3-hydroxy-2,2-dimethyl-propyl, 2,2,2-trifluoroethyl, 3,3,3-trifluoro-propyl, or 2,2,3,3,3-pentafluoro-propyl.

In another embodiment, one $R^W$ is hydrogen and the other $R^W$ is an optionally substituted C3-C7 cycloaliphatic or a heterocycloaliphatic ring having up to three heteroatoms selected from O, N, or S, wherein said ring is optionally fused to one or more phenyl or heteroaryl ring. Exemplary rings include cyclopentyl, cyclohexyl, cyclohexenyl, cycloheptyl, tetrahydro-2H-pyranyl, tetrahydro-2H-thiopyranyl, 9H-fluoren-9-yl or piperidinyl.

In another embodiment, two $R^W$, taken together with the carbon atom that they are attached to, form an optionally substituted 3-9 membered cycloaliphatic or heterocyclic, monocyclic, bicyclic, or tricyclic ring. Exemplary embodiments include 9H-fluoroen-9-yl, tetrahydro-2H-pyran-4-yl, tetrahydro-2H-thiopyran-4-yl, cyclopropyl, cyclobutyl, cyclopentyl, cyclohexyl, cycloheptyl, cyclohexenyl, piperidinyl, or 1-benzyl-piperidin-4-yl.

In one embodiment, $R^A$ is hydrogen. Or, $R^A$ is C1-C6 aliphatic, optionally substituted with up to 4 $R^1$ substituents. Or, $R^A$ is C1-C6 heteroaliphatic, optionally substituted with up to 4 $R^1$ substituents. Exemplary $R^A$ includes C1-C6 alkyl (e.g., methyl, ethyl, propyl, or butyl), C1-C6 heteroalkyl, C(O)—C1-C6 alkyl, C(O)—C1-C6 heteroalkyl.

In one embodiment, Q is a bond. Or, Q is a C1-C6 aliphatic chain wherein up to two non-adjacent methylene units of Q are optionally replaced by CO, CO$_2$, CONR, OCONR, NRCO, NRCO$_2$, NRCONR, SO, SO$_2$, NRSO$_2$, SO$_2$NR, NRSO$_2$NR, O, S, or NR, wherein R is hydrogen or C1-C6 alkyl.

In another embodiment, each $R^M$ is independently R'.

Or, $R^M$ is selected from halogen, NO$_2$, CN, OR', SR', N(R')$_2$, NR'C(O)R', NR'C(O)N(R')$_2$, NR'CO$_2$R', C(O)R', CO$_2$R', OC(O)R', C(O)N(R')$_2$, OC(O)N(R')$_2$, SOR', SO$_2$R', SO$_2$N(R')$_2$, NR'SO$_2$R', NR'SO$_2$N(R')$_2$, C(O)C(O)R', or C(O)CH$_2$C(O)R'.

In one embodiment, R' is hydrogen.

In one embodiment, R' is a C1-C8 aliphatic group, optionally substituted with up to 3 substituents selected from halo, CN, CF$_3$, CHF$_2$, OCF$_3$, or OCHF$_2$, wherein up to two methylene units of said C1-C8 aliphatic is optionally replaced with —CO—, —CONH(C1-C4 alkyl)-, —CO$_2$—, —OCO—, —N(C$_1$-C$_4$alkyl)CO$_2$—, —O—, —N(C$_1$-C$_4$alkyl)CON(C$_1$-C$_4$ alkyl)-, —OCON(C1-C4 alkyl)-, —N(C1-C4 alkyl)CO—, —S—, —N(C1-C4 alkyl)-, —SO$_2$N(C1-C4 alkyl)-, N(C1-C4 alkyl)SO$_2$—, or —N(C1-C4 alkyl)SO$_2$N(C1-C4 alkyl)-.

In one embodiment, R' is a 3-8 membered saturated, partially unsaturated, or fully unsaturated monocyclic ring having 0-3 heteroatoms independently selected from nitrogen, oxygen, or sulfur, wherein R' is optionally substituted with up to 3 substituents selected from halo, CN, CF$_3$, CHF$_2$, OCF$_3$, OCHF$_2$, or C1-C6 alkyl, wherein up to two methylene units of said C1-C6 alkyl is optionally replaced with —CO—, —CONH(C1-C4 alkyl)-, —CO$_2$—, —OCO—, —N(C1-C4 alkyl)CO$_2$—, —O—, —N(C1-C4 alkyl)CON(C1-C4 alkyl)-, —OCON(C1-C4 alkyl)-, —N(C1-C4 alkyl)CO—, —S—, —N(C1-C4 alkyl)-, —SO$_2$N(C1-C4 alkyl)-, N(C1-C4 alkyl)SO$_2$—, or —N(C1-C4 alkyl)SO$_2$N(C1-C4 alkyl)-.

In one embodiment, R' is an 8-12 membered saturated, partially unsaturated, or fully unsaturated bicyclic ring system having 0-5 heteroatoms independently selected from nitrogen, oxygen, or sulfur; wherein R' is optionally substituted with up to 3 substituents selected from halo, CN, CF$_3$, CHF$_2$, OCF$_3$, OCHF$_2$, or C$_1$-C$_6$ alkyl, wherein up to two methylene units of said C1-C6 alkyl is optionally replaced with —CO—, —CONH(C1-C4 alkyl)-, —CO$_2$—, —OCO—, —N(C1-C4 alkyl)CO$_2$—, —O—, —N(C1-C4 alkyl)CON(C1-C4 alkyl)-, —OCON(C1-C4 alkyl)-, —N(C1-C4 alkyl)CO—, —S—, —N(C1-C4 alkyl)-, —SO$_2$N(C1-C4 alkyl)-, N(C1-C4 alkyl)SO$_2$—, or —N(C1-C4 alkyl)SO$_2$N(C1-C4 alkyl)-.

In one embodiment, two occurrences of R' are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur, wherein R' is optionally substituted with up to 3 substituents selected from halo, CN, CF$_3$, CHF$_2$, OCF$_3$, OCHF$_2$, or C1-C6 alkyl, wherein up to two methylene units of said C1-C6 alkyl is optionally replaced with —CO—, —CONH(C1-C4 alkyl)-, —CO$_2$—, —OCO—, —N(C1-C4 alkyl)CO$_2$—, —O—, —N(C1-C4 alkyl)CON(C1-C4 alkyl)-, —OCON(C1-C4 alkyl)-, —N(C1-C4 alkyl)CO—, —S—, —N(C1-C4 alkyl)-, —SO$_2$N(C1-C4 alkyl)-, N(C1-C4 alkyl)SO$_2$—, or —N(C1-C4 alkyl)SO$_2$N(C1-C4 alkyl)-.

In one embodiment, ring A is:

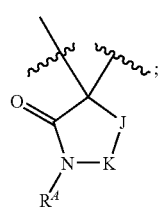

(a)

wherein:

$R^1$ is as defined above;

J is selected from C(O), $C(R^5)_2$, =N—, —$NR^{6b}$, or =$CR^{6a}$;

K is selected from C(O), SO2, =N—, —$NR^{6b}$, =$CR^{6b}$, or $C(R^5)_2$;

each $R^5$ is independently hydrogen, C1-C6 aliphatic optionally substituted with up to 5 substituents selected from oxo, halo, —OH, —O—C1-C6 aliphatic, $NH_2$, NH(C1-C6 aliphatic), or N(C1-C6 aliphatic)$_2$;

each $R^{6a}$ and $R^{6b}$ is independently selected from hydrogen, halo, CN, —OH, —O—$C_1$-$C_6$ aliphatic, $NH_2$, NH(C1-C6 aliphatic), or N(C1-C6 aliphatic)$_2$, C1-C6 aliphatic optionally substituted with up to 5 substituents selected from oxo, halo, —OH, —O—C1-C6 aliphatic, $NH_2$, NH(C1-C6 aliphatic), or N(C1-C6 aliphatic)$_2$, phenyl optionally substituted with up to 5 Q—$R^M$ substituents, or a 5-7 membered heterocycle or heteroaryl ring having up to 4 heteroatoms selected from O, N, S, SO, or $SO_2$, wherein said heterocycle or heteroaryl ring is optionally substituted with up to 5 Q—$R^M$ substituents; or $R^{6a}$ and $R^{6b}$ and the atoms to which they are attached are joined to form a ring selected from cyclopentyl, cyclohexyl, cyclopentenyl, cyclohexenyl, phenyl, pyridyl, pyrimidinyl, pyrazinyl, pyridazinyl, furanyl, dihydrofuranyl, dihydropyranyl, thiazolyl, isothiazolyl, oxazolyl, isoxazolyl, imidazolyl, triazolyl, thienyl, dihydrothienyl, or dihydrothiopyranyl, wherein said ring is optionally substituted with up to 5 Q—$R^M$ substituents.

In one embodiment, ring A is selected from:

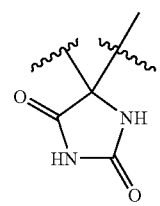

a-i

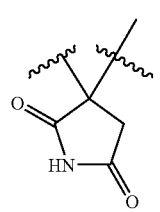

a-ii

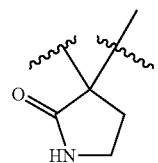

a-iii

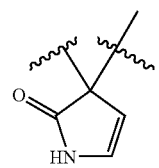

a-iv

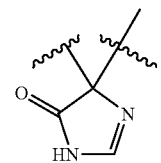

a-v

In another embodiment, ring A is selected from:

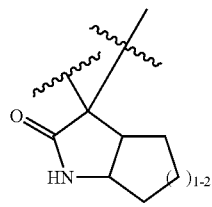

a-vi

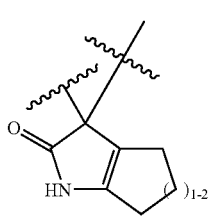

a-vii

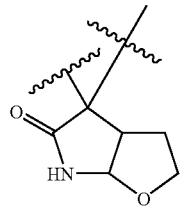

a-viii

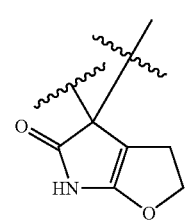

a-ix

-continued
a-x 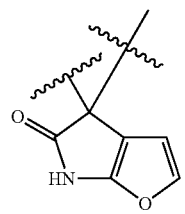
a-xi 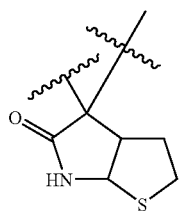
a-xii 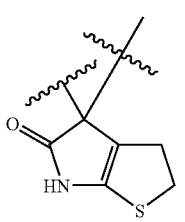
a-xiii 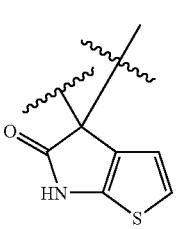
a-xiv 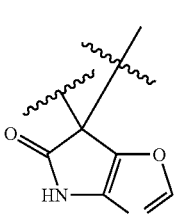
a-xv 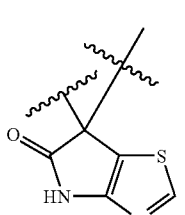
a-xvi 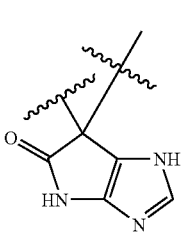
-continued
a-xvii 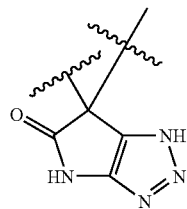
In another embodiment, ring A is selected from:
a-xviii 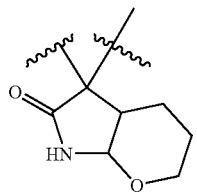
a-xix 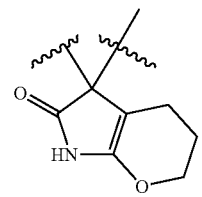
a-xx 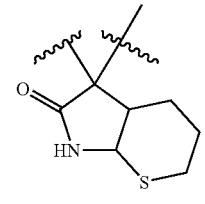
a-xxi 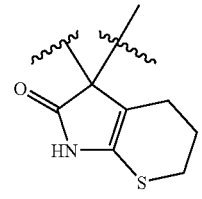
In another embodiment, ring A is selected from:
a-xxii 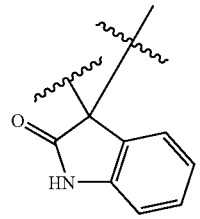

-continued
a-xxiii
a-xxiv
a-xxv
a-xxvi
a-xxvii
a-xxviii
a-xxix
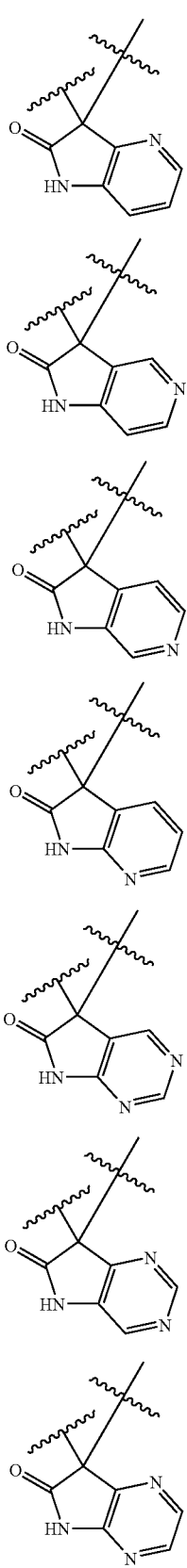
In one embodiment, Ring A is a-i.
In one embodiment, the present invention provides compounds of formula I-A or I-B:
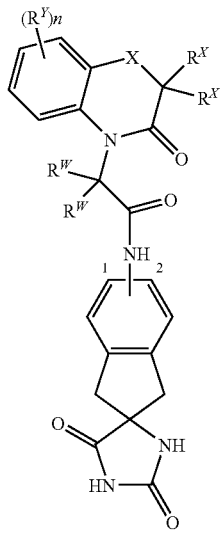
(I-A)
or
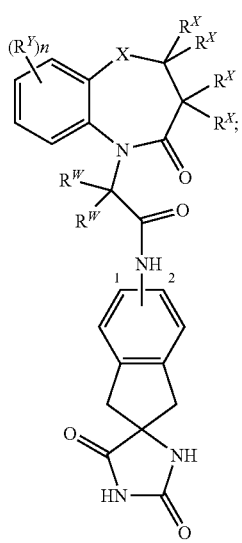
(I-B)
wherein:
n, $R^X$, $R^Y$, $R^W$, and X are as defined above and the
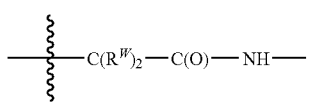
group is attached to the phenyl ring at carbon atom 1 or 2.

In another embodiment, the present invention provides compounds of formula I':

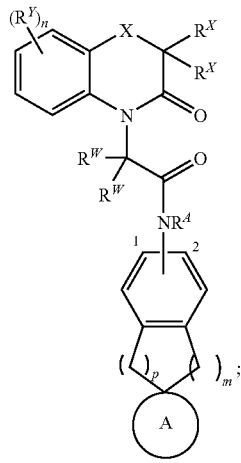

or a pharmaceutically acceptable salt thereof, wherein:
said $NR^A$ group is attached to the phenyl ring at carbon atom 1 or 2;

X is O, $NR^A$, S, SO, or $SO_2$;

$R^A$ is hydrogen or C1-C6 aliphatic optionally substituted with up to 4 $R^1$ substituents;

ring A is a 4-7 membered heterocyclic ring having 1-4 heteroatoms selected from O, N, S, SO, or $S(O)_2$, wherein said heterocyclic ring is optionally fused to a phenyl or a 5-7 membered heterocyclic or heteroaryl ring having 1-4 heteroatoms selected from O, N, S, SO, or $S(O)_2$; wherein ring A has at least one oxo substituent;

wherein ring A, together with the optionally fused ring, is optionally substituted with up to 5 $R^2$ substituents;

m is 1-3;
p is 1-3;
n is 1-4;

each $R^X$ is independently hydrogen, halo, aryl, heteroaryl, C1-C6 aliphatic, C1-C6 heteroaliphatic, aryl-C1-C6 aliphatic, aryl-C1-C6 heteroaliphatic, heteroaryl-C1-C6 aliphatic, heteroaryl-C1-C6 heteroaliphatic, wherein $R^X$ is optionally substituted with up to 5 $R^3$ substituents; or two $R^X$, taken together with the carbon atom that they are attached to, form a 3-9 membered cycloaliphatic or heterocyclic ring, wherein said heterocyclic ring has up to 3 heteroatoms selected from O, S, and N; wherein said ring is optionally substituted with up to 3 $R^3$ substituents;

each $R^W$ is independently hydrogen, halo, aryl, heteroaryl, C1-C6 aliphatic, C1-C6 heteroaliphatic, aryl-C1-C6 aliphatic, heteroaryl-C1-C6 aliphatic, wherein $R^X$ is optionally substituted with up to 5 $R^4$ substituents; or two $R^W$, taken together with the carbon atom that they are attached to, form a 3-9 membered cycloaliphatic or heterocyclic ring, wherein said heterocyclic ring has up to 3 heteroatoms selected from O, S, and N; wherein said ring is optionally substituted with up to 3 $R^4$ substituents;

wherein each occurrence of $R^1$, $R^2$, $R^3$, $R^4$, and $R^Y$ is independently Q—$R^M$;

wherein Q is a bond or is a $C_1$-$C_6$ aliphatic chain wherein up to two non-adjacent methylene units of Q are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR;

wherein each occurrence of $R^M$ is independently selected from R', halogen, $NO_2$, CN, OR', SR', N(R')$_2$, NR'C(O)R', NR'C(O)N(R')$_2$, NR'$CO_2$R', C(O)R', $CO_2$R', OC(O)R', C(O)N(R')$_2$, OC(O)N(R')$_2$, SOR', $SO_2$R', $SO_2$N(R')$_2$, NR'$SO_2$R', NR'$SO_2$N(R')$_2$, C(O)C(O)R', or C(O)CH$_2$C(O)R', wherein each occurrence of R is independently selected from hydrogen or an optionally substituted C1-C6 aliphatic group or C1-C6 heteroaliphatic;

wherein each occurrence of R' is independently selected from hydrogen or an optionally substituted group selected from $C_{1-8}$ aliphatic, $C_{6-10}$ aryl, a heteroaryl ring having 5-10 ring atoms, or a heterocyclyl ring having 3-10 ring atoms, or wherein R and R' taken together with the atom(s) to which they are bound, or two occurrences of R' taken together with the atom(s) to which they are bound, form a 3-8 membered cycloalkyl, heterocyclyl, aryl, or heteroaryl ring having 0-3 heteroatoms independently selected from nitrogen, oxygen, or sulfur.

In one embodiment of formula I', m is 1 and p is 1. In another embodiment, m is 1 and p is 2. Or, m is 2 and p is 1. Or, m is 2 and p is 2.

In one embodiment of formula I', ring A is:

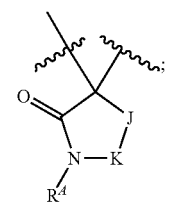

(a)

wherein:
$R^A$ is as defined above;

J is selected from C(O), C($R^5$)$_2$, =N—, —$NR^{6b}$, or =$CR^{6a}$;

K is selected from C(O), SO2, =N—, —$NR^{6b}$, =$CR^{6b}$, or C($R^5$)$_2$;

each $R^5$ is independently hydrogen, C1-C6 aliphatic optionally substituted with up to 5 substituents selected from oxo, halo, —OH, —O—C1-C6 aliphatic, $NH_2$, NH(C1-C6 aliphatic), or N($C_1$-$C_6$ aliphatic)$_2$;

each $R^{6a}$ and $R^{6b}$ is independently selected from hydrogen, halo, CN, —OH, —O—C1-C6 aliphatic, $NH_2$, NH(C1-C6 aliphatic), or N(C1-C6 aliphatic)$_2$, C1-C6 aliphatic optionally substituted with up to 5 substituents selected from oxo, halo, —OH, —O—C1-C6 aliphatic, $NH_2$, NH(C1-C6 aliphatic), or N(C1-C6 aliphatic)$_2$, phenyl optionally substituted with up to 5 Q—$R^M$ substituents, or a 5-7 membered heterocycle or heteroaryl ring having up to 4 heteroatoms selected from O, N, S, SO, or $SO_2$, wherein said heterocycle or heteroaryl ring is optionally substituted with up to 5 Q—$R^M$ substituents; or $R^{6a}$ and $R^{6b}$ and the atoms to which they are attached are joined to form a ring selected from cyclopentyl, cyclohexyl, cyclopentenyl, cyclohexenyl, phenyl, pyridyl, pyrimidinyl, pyrazinyl, pyridazinyl, furanyl, dihydrofuranyl, dihydropyranyl, thiazolyl, isothiazolyl, oxazolyl, isoxazolyl, imidazolyl, triazolyl, thienyl, dihyrothienyl, or dihydrothiopyranyl, wherein said ring is optionally substituted with up to 5 Q—$R^M$ substituents.

In one embodiment of formula I', ring A is selected from:

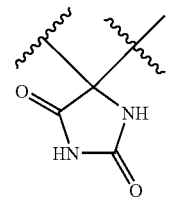
a-i
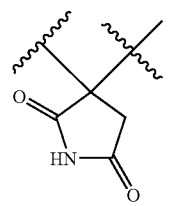
a-ii
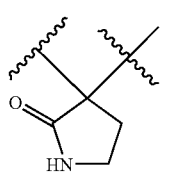
a-iii
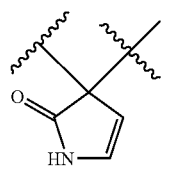
a-iv
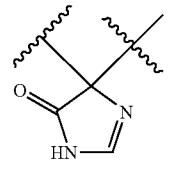
a-v
In another embodiment of formula I', ring A is selected from:
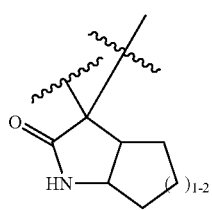
a-vi
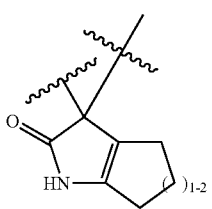
a-vii
-continued
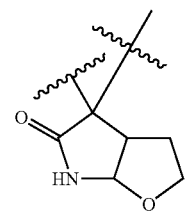
a-viii
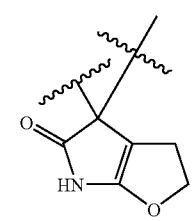
a-ix
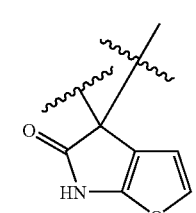
a-x
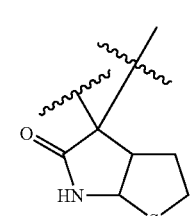
a-xi
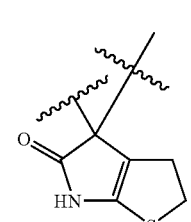
a-xii
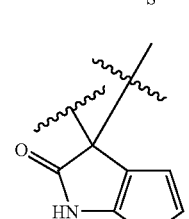
a-xiii
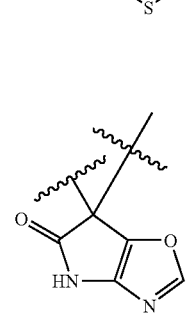
a-xiv -continued
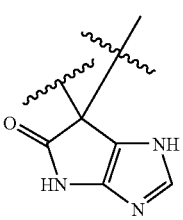
a-xv
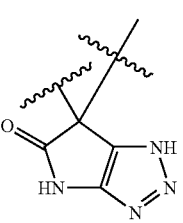
a-xvi
a-xvii
In another embodiment of formula I', ring A is selected from:
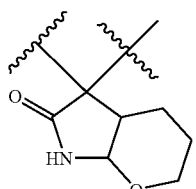
a-xviii
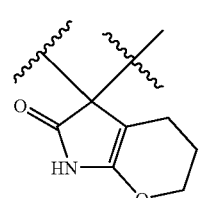
a-xix
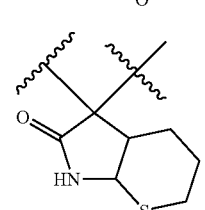
a-xx
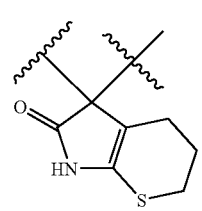
a-xxi
In another embodiment of formula I', ring A is selected from:
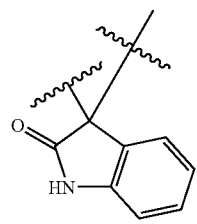
a-xxii
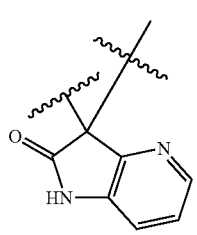
a-xxiii
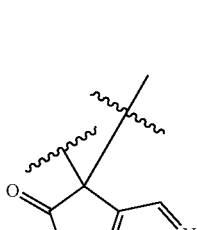
a-xxiv
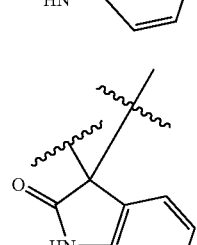
a-xxv
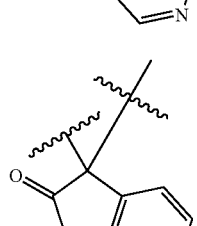
a-xxvi
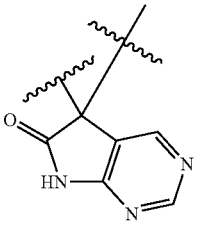
a-xxvii

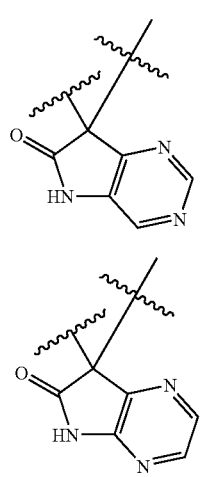

a-xxviii

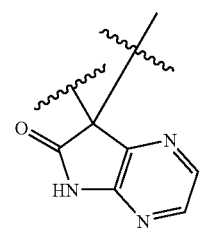

a-xxix

In one embodiment of formula I', Ring A is a-i.

In one embodiment of any of formulae I-A, I-B, or I', X is O, NRA, S, SO, or SO₂ and Y is a bond, C(R$^X$)₂, or —C(R$^X$)₂—C(R$^X$)₂—.

In one embodiment of any of formulae I-A, I-B, or I', X is O or S.

In one embodiment of any of formulae I-A, I-B, or I', Y is a bond.

In another embodiment of any of formulae I-A, I-B, or I', Y is C(R$^X$)₂. In another embodiment, Y is —CH₂—

In yet another embodiment of any of formulae I-A, I-B, or I', Y is —C(R$^X$)₂—C(R$^X$)₂—. Or, Y is —CH₂—CH₂—.

In one embodiment of any of formulae I-A, I-B, or I', each R$^X$ is hydrogen.

In one embodiment of any of formulae I-A, I-B, or I', at least one R$^X$ is C1-C6 aliphatic optionally substituted with one or more halo, OH, C1-C4 alkoxy, C1-C4 alkoxy carbonyl, or di-(C1-C4 alkyl)amino. Exemplary embodiments include methyl, ethyl, propyl, isopropyl, butyl, t-butyl, 3,3-dimethyl-butyl, 3-methyl-butyl, 2-methyl-propyl, 2-methoxy-ethyl, 3-ethoxypropyl, 1-(methoxy carbonyl)-3-methyl-butyl, 1-(hydroxy methyl)-3-methyl-butyl, allyl, acetenyl, 2-(diethylamino)ethyl, 1-methyl-2-methoxy-ethyl, 3-hydroxy-2,2-dimethyl-propyl, 2,2,2-trifluoroethyl, 3,3,3-trifluoro-propyl, or 2,2,3,3,3-pentafluoro-propyl. In a further embodiment, the one or more other R$^X$ is hydrogen.

In another embodiment of any of formulae I-A, I-B, or I', at least one R$^X$ is phenyl or heteroaryl optionally substituted with one or more substituents independently selected from C1-C6 aliphatic, cyano, halo, halo-C1-C6 aliphatic, aryl-C1-C6 aliphatic, heteroaryl-C1-C6 aliphatic, aralkyloxy, di(C1-C6 aliphatic)amino, O—C1-C6 aliphatic, S(O)—C1-C6 aliphatic, or S(O)₂—C1-C6 aliphatic. In a further embodiment, the one or more other R$^X$ is hydrogen.

In another embodiment of any of formulae I-A, I-B, or I', at least one R$^X$ is an optionally substituted C3-C7 cycloaliphatic or a heterocycloaliphatic ring having up to three heteroatoms selected from O, N, or S, wherein said ring is optionally fused to one or more phenyl or heteroaryl ring. Exemplary rings include cyclopentyl, cyclohexyl, cyclohexenyl, cycloheptyl, tetrahydro-2H-pyranyl, tetrahydro-2H-thiopyranyl, 9H-fluoren-9-yl or piperidinyl. In a further embodiment, the one or more other R$^X$ is hydrogen.

In another embodiment of any of formulae I-A, I-B, or I', two R$^X$, taken together with the carbon atom that they are attached to, form an optionally substituted 3-9 membered cycloaliphatic or heterocyclic, monocyclic, bicyclic, or tricyclic ring. Exemplary embodiments include 9H-fluroen-9-yl, tetrahydro-2H-pyran-4-yl, tetrahydro-2H-thiopyran-4-yl, cyclopropyl, cyclobutyl, cyclopentyl, cyclohexyl, cyclohexenyl, piperidinyl, or 1-benzyl-piperidin-4-yl.

In another embodiment of any of formulae I-A, I-B, or I', at least one R$^X$ is —C(O)NH—R$^M$, —OC(O)—R$^M$, —NHC(O)—R$^M$, —NHC(O)O—R$^M$, wherein R$^M$ is an optionally substituted phenyl, heteroaryl or heterocyclic group. In a further embodiment, the one or more other R$^X$ is hydrogen.

In one embodiment of any of formulae I-A, I-B, or I', both R$^W$ are hydrogen.

In one embodiment of any of formulae I-A, I-B, or I', one R$^W$ is hydrogen and the other R$^W$ is C1-C6 aliphatic optionally substituted with one or more halo, OH, C1-C4 alkoxy, C1-C4 alkoxy carbonyl, or di-(C1-C4 alkyl)amino. Exemplary embodiments include methyl, ethyl, propyl, isopropyl, butyl, t-butyl, 3,3-dimethyl-butyl, 3-methyl-butyl, 2-methyl-propyl, 2-methoxy-ethyl, 3-ethoxypropyl, 1-(methoxy carbonyl)-3-methyl-butyl, 1-(hydroxy methyl)-3-methyl-butyl, allyl, acetenyl, 2-(diethylamino)ethyl, 1-methyl-2-methoxy-ethyl, 3-hydroxy-2,2-dimethyl-propyl, 2,2,2-trifluoroethyl, 3,3,3-trifluoro-propyl, or 2,2,3,3,3-pentafluoro-propyl.

In another embodiment of any of formulae I-A, I-B, or I', one R$^W$ is hydrogen and the other R$^W$ is an optionally substituted C3-C7 cycloaliphatic or a heterocycloaliphatic ring having up to three heteroatoms selected from O, N, or S, wherein said ring is optionally fused to one or more phenyl or heteroaryl ring. Exemplary rings include cyclopentyl, cyclohexyl, cyclohexenyl, cycloheptyl, tetrahydro-2H-pyranyl, tetrahydro-2H-thiopyranyl, 9H-fluoren-9-yl or piperidinyl.

In another embodiment of any of formulae I-A, I-B, or I', two R$^W$, taken together with the carbon atom that they are attached to, form an optionally substituted 3-9 membered cycloaliphatic or heterocyclic, monocyclic, bicyclic, or tricyclic ring. Exemplary embodiments include 9H-fluroen-9-yl, tetrahydro-2H-pyran-4-yl, tetrahydro-2H-thiopyran-4-yl, cyclopropyl, cyclobutyl, cyclopentyl, cyclohexyl, cyclohexenyl, piperidinyl, or 1-benzyl-piperidin-4-yl.

In one embodiment of any of formulae I-A, I-B, or I', R$^A$ is hydrogen. Or, R$^A$ is C1-C6 aliphatic, optionally substituted with up to 4 R$^1$ substituents. Or, R$^A$ is C1-C6 heteroaliphatic, optionally substituted with up to 4 R$^1$ substituents. Exemplary R$^A$ includes C1-C6 alkyl (e.g., methyl, ethyl, propyl, or butyl), C1-C6 heteroalkyl, C(O)—C1-C6 alkyl, C(O)—C1-C6 heteroalkyl.

In one embodiment of any of formulae I-A, I-B, or I', Q is a bond. Or, Q is a C₁-C₆ aliphatic chain wherein up to two non-adjacent methylene units of Q are optionally replaced by CO, CO₂, CONR, OCONR, NRCO, NRCO₂, NRCONR, SO, SO₂, NRSO₂, SO₂NR, NRSO₂NR, O, S, or NR, wherein R is hydrogen or C1-C6 alkyl.

In another embodiment of any of formulae I-A, I-B, or I', each R$^M$ is independently R'.

Or, R$^M$ is selected from halogen, NO₂, CN, OR', SR', N(R')₂, NR'C(O)R', NR'C(O)N(R')₂, NR'CO₂R', C(O)R', CO₂R', OC(O)R', C(O)N(R')₂, OC(O)N(R')₂, SOR', SO₂R', SO₂N(R')₂, NR'SO₂R', NR'SO₂N(R')₂, C(O)C(O)R', or C(O)CH₂C(O)R'.

In one embodiment of any of formulae I-A, I-B, or I', R' is hydrogen.

In one embodiment of any of formulae I-A, I-B, or I', R' is a C1-C8 aliphatic group, optionally substituted with up to 3 substituents selected from halo, CN, CF₃, CHF₂, OCF₃, or OCHF₂, wherein up to two methylene units of said C1-C8 aliphatic is optionally replaced with —CO—, —CONH(C1-C4 alkyl)-, —CO₂—, —OCO—, —N(C1-C4 alkyl)CO₂—, —O—, —N(C1-C4 alkyl)CON(C1-C4 alkyl)-, —OCON(C1-C4 alkyl)-, —N(C1-C4 alkyl)CO—, —S—, —N(C1-C4 alkyl)-, —SO₂N(C1-C4 alkyl)-, N(C1-C4 alkyl)SO₂— or —N(C1-C4 alkyl)SO₂N(C1-C4 alkyl)-.

In one embodiment of any of formulae I-A, I-B, or I', R' is a 3-8 membered saturated, partially unsaturated, or fully unsaturated monocyclic ring having 0-3 heteroatoms independently selected from nitrogen, oxygen, or sulfur, wherein R' is optionally substituted with up to 3 substituents selected from halo, CN, $CF_3$, $CHF_2$, $OCF_3$, $OCHF_2$, or C1-C6 alkyl, wherein up to two methylene units of said C1-C6 alkyl is optionally replaced with —CO—, —CONH(C1-C4 alkyl)-, —$CO_2$—, —OCO—, —N(C1-C4 alkyl)$CO_2$—, —O—, —N(C1-C4 alkyl)CON(C1-C4 alkyl)-, —OCON(C1-C4 alkyl)-, —N(C1-C4 alkyl)CO—, —S—, —N(C1-C4 alkyl)-, —$SO_2$N(C1-$C_4$ alkyl)-, N($C_1$-$C_4$ alkyl)$SO_2$—, or —N(C1-C4 alkyl)$SO_2$N(C1-C4 alkyl)-.

In one embodiment of any of formulae I-A, I-B, or I', R' is an 8-12 membered saturated, partially unsaturated, or fully unsaturated bicyclic ring system having 0-5 heteroatoms independently selected from nitrogen, oxygen, or sulfur; wherein R' is optionally substituted with up to 3 substituents selected from halo, CN, $CF_3$, $CHF_2$, $OCF_3$, $OCHF_2$, or C1-C6 alkyl, wherein up to two methylene units of said C1-C6 alkyl is optionally replaced with —CO—, —CONH(C1-C4 alkyl)-, —$CO_2$—, —OCO—, —N(C1-C4 alkyl)$CO_2$—, —O—, —N(C1-C4 alkyl)CON(C1-C4 alkyl)-, —OCON(C1-C4 alkyl)-, —N(C1-C4 alkyl)CO—, —S—, —N(C1-C4 alkyl)-, —$SO_2$N(C1-C4 alkyl)-, N(C1-C4 alkyl)$SO_2$—, or —N(C1-C4 alkyl)$SO_2$N(C1-C4 alkyl)-.

In one embodiment of any of formulae I-A, I-B, or I', two occurrences of R' are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur, wherein R' is optionally substituted with up to 3 substituents selected from halo, CN, $CF_3$, $CHF_2$, $OCF_3$, $OCHF_2$, or C1-C6 alkyl, wherein up to two methylene units of said C1-C6 alkyl is optionally replaced with —CO—, —CONH(C1-C4 alkyl)-, —$CO_2$—, —OCO—, —N(C1-C4 alkyl)$CO_2$—, —O—, —N(C1-C4 alkyl)CON(C1-C4 alkyl)-, —OCON(C1-C4 alkyl)-, —N(C1-C4 alkyl)CO—, —S—, —N(C1-C4 alkyl)-, —$SO_2$N(C1-C4 alkyl)-, N(C1-C4 alkyl)$SO_2$—, or —N(C1-C4 alkyl)$SO_2$N(C1-C4 alkyl)-.

Exemplary compounds of the present invention are shown below in Tables 1-4 below.

TABLE 1

1

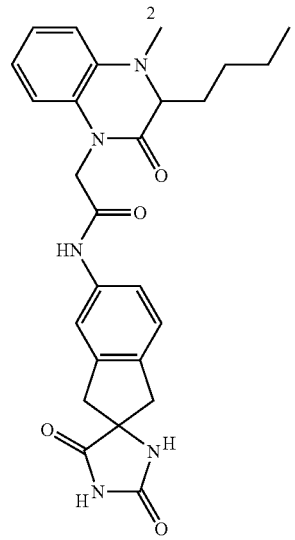

TABLE 1-continued

2

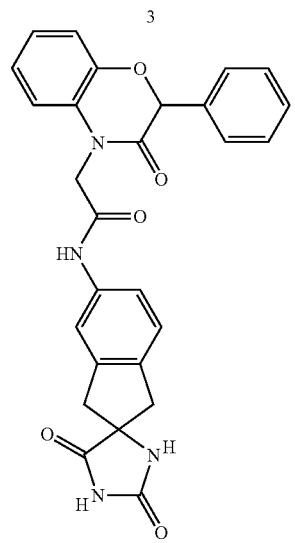

3

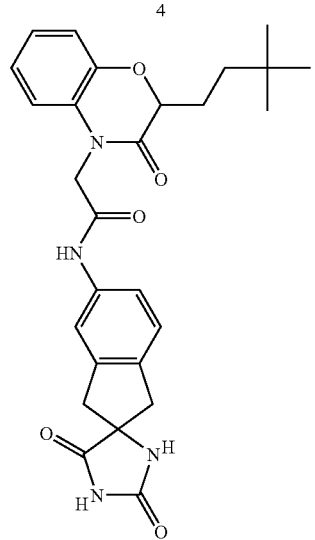

4

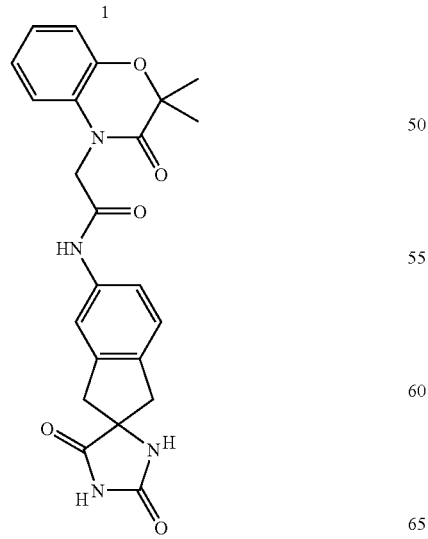

TABLE 1-continued
5
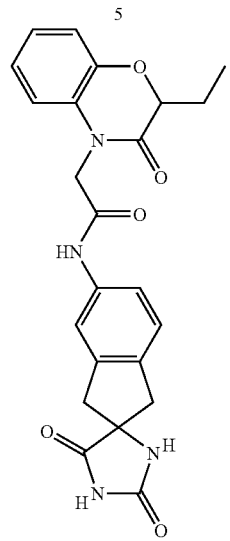
6
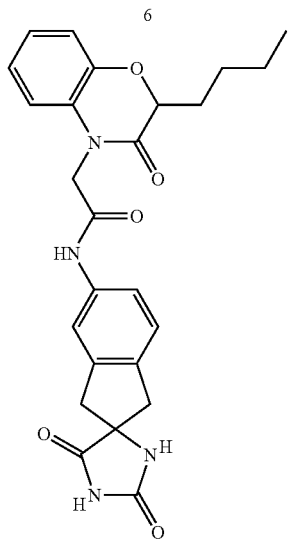
7
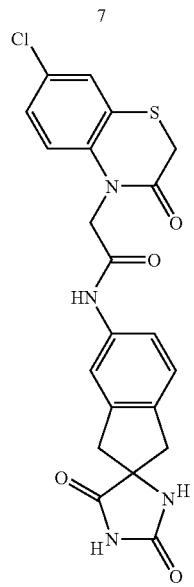
TABLE 1-continued
8
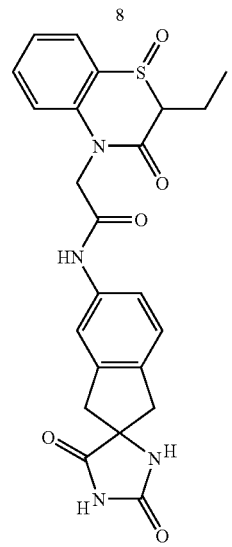
9
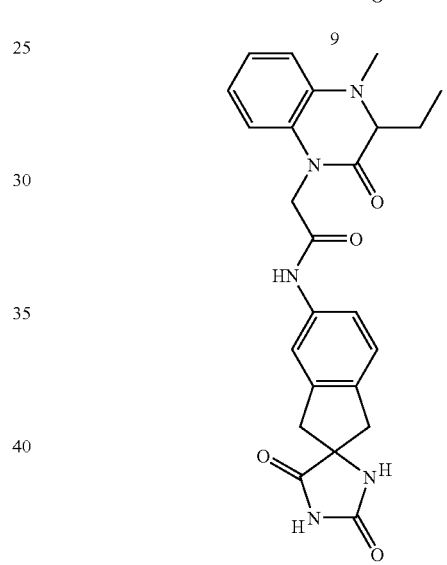
10
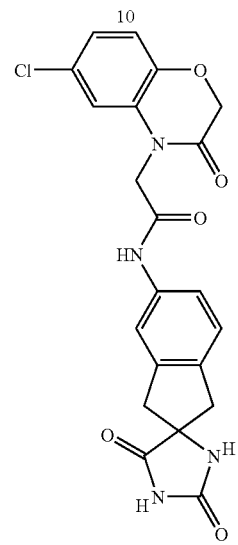

TABLE 1-continued
11
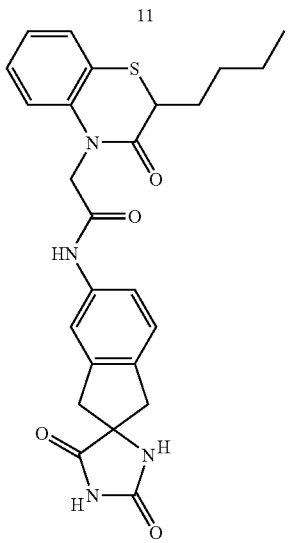
12
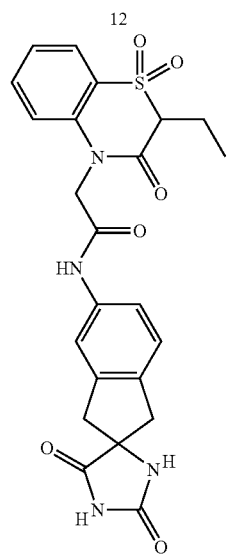
13
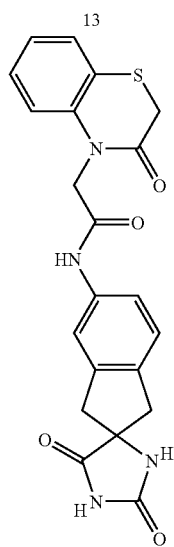
TABLE 1-continued
14
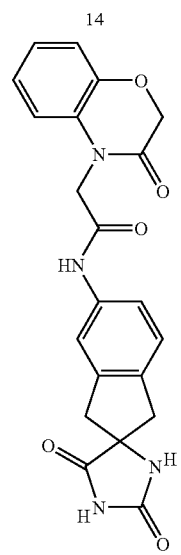
15
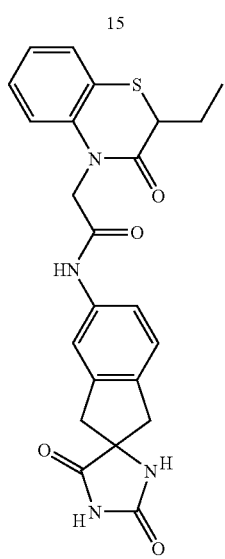

TABLE 2
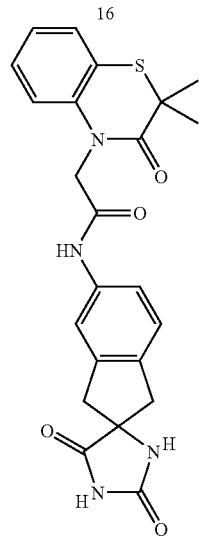
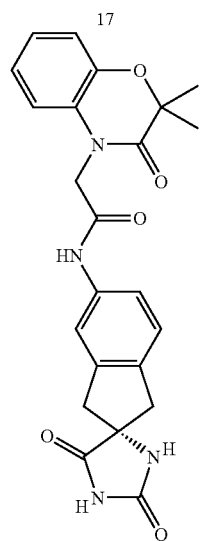
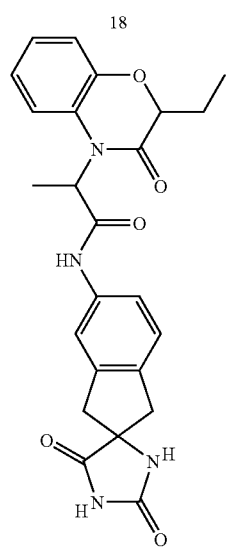
TABLE 2-continued
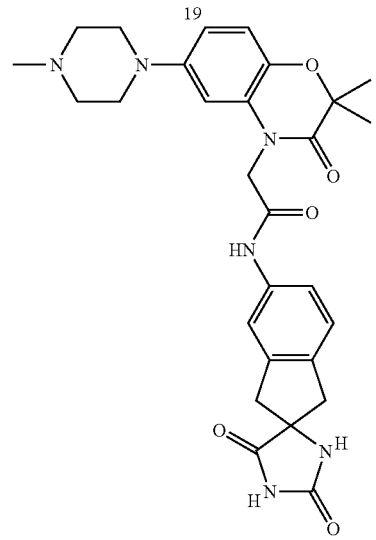
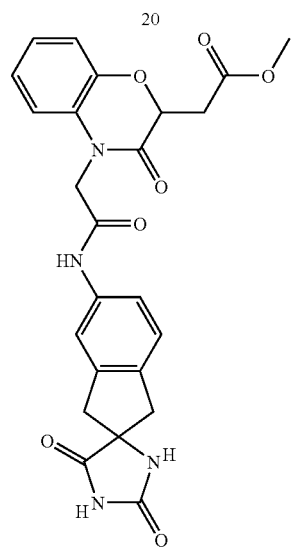
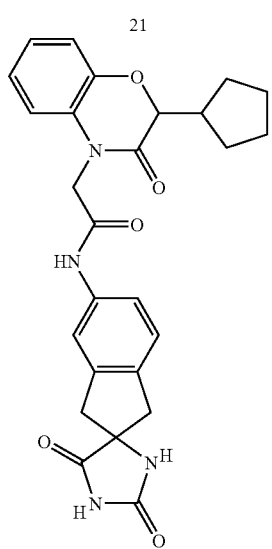

TABLE 2-continued
22
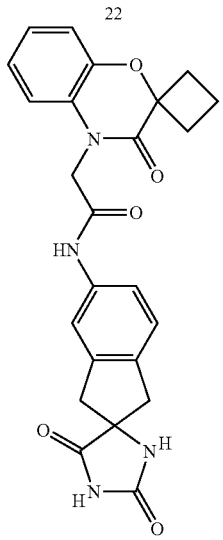
23
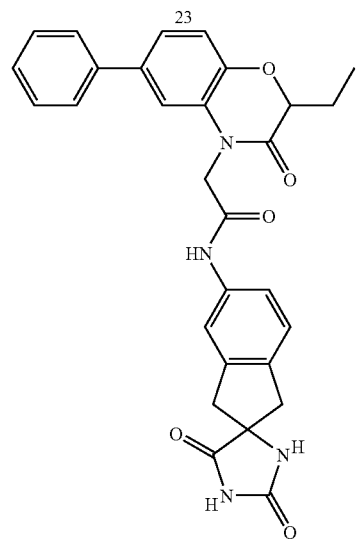
24
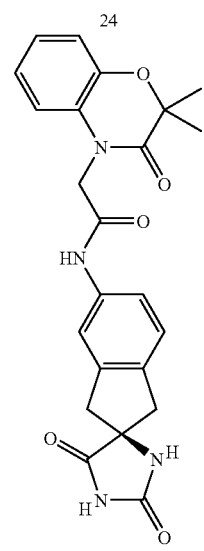
TABLE 2-continued
25
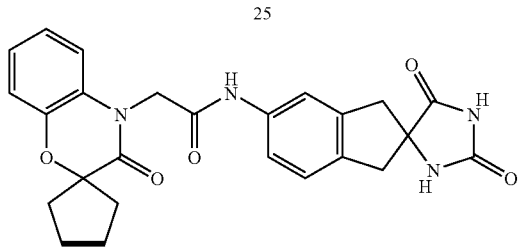
26
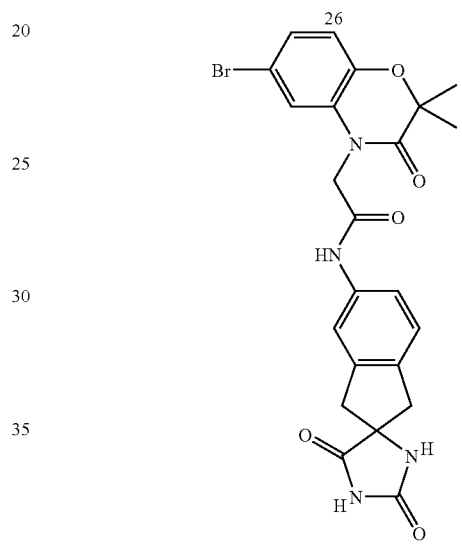
27
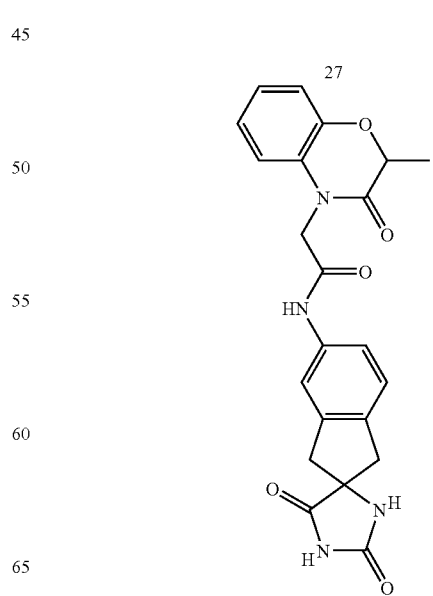

TABLE 2-continued
28
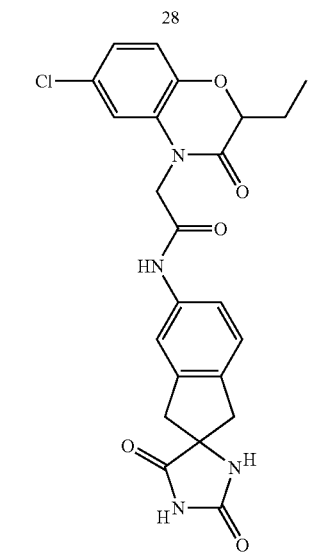
29
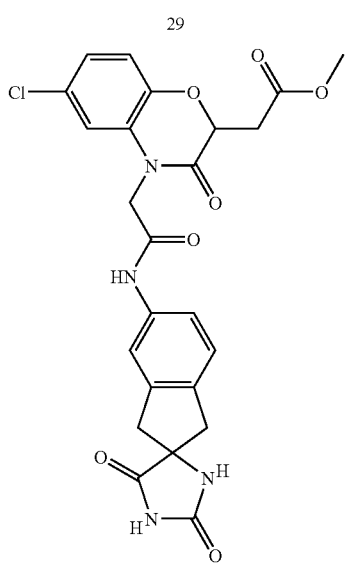
30
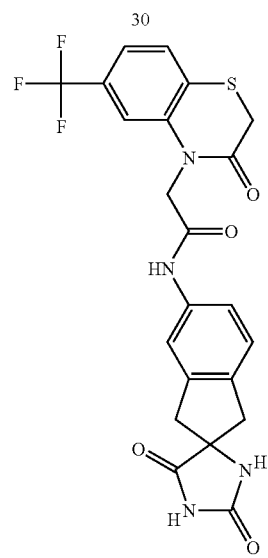
31
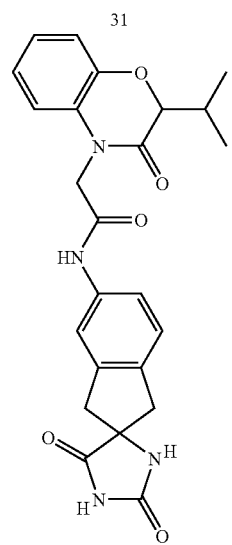
32
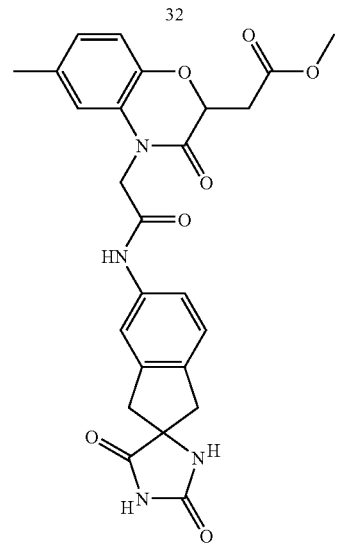

TABLE 2-continued
33
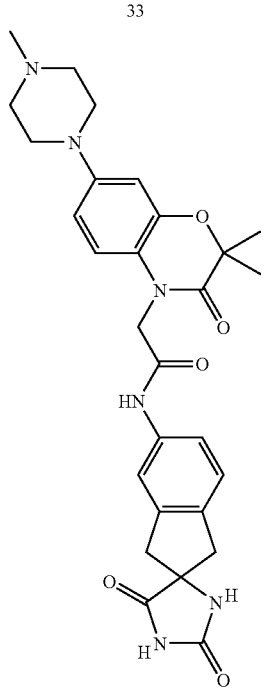
34
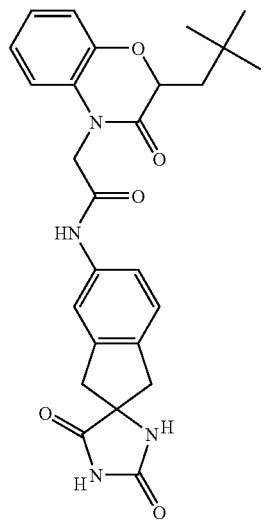
TABLE 2-continued
35
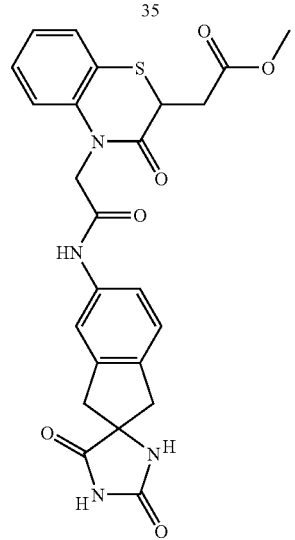
36
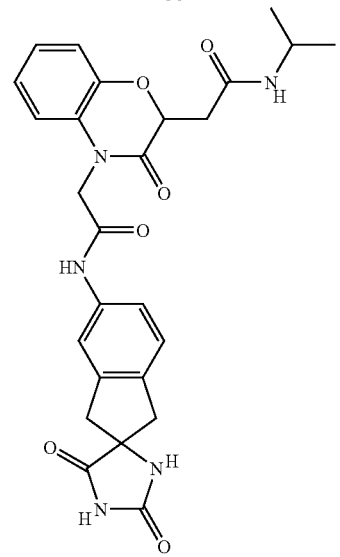
37
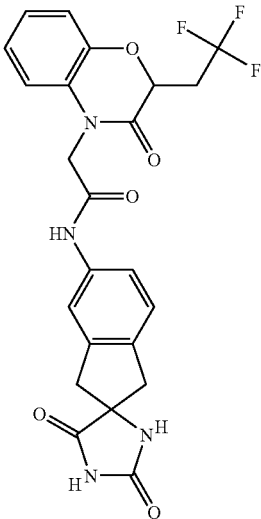

TABLE 2-continued
38
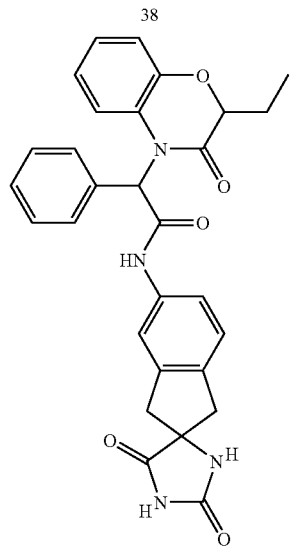
39
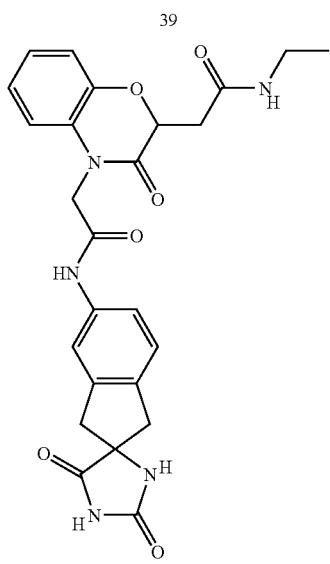
TABLE 2-continued
40
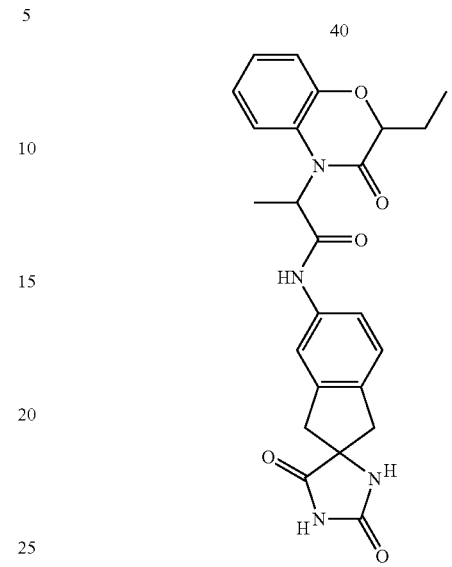
41
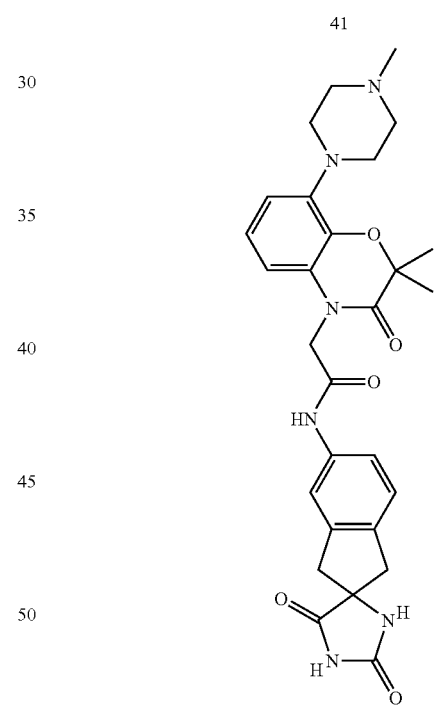
42
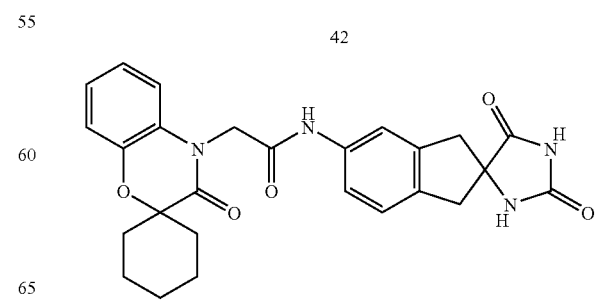

TABLE 2-continued
43
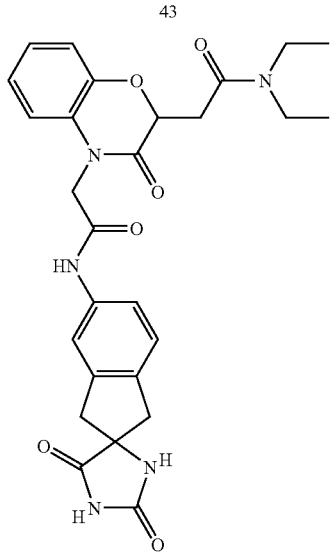
44
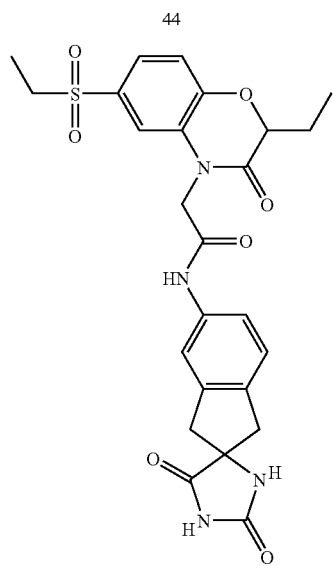
TABLE 2-continued
45
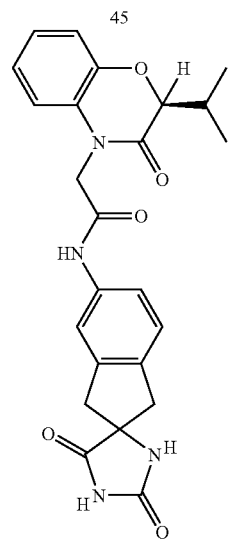
46
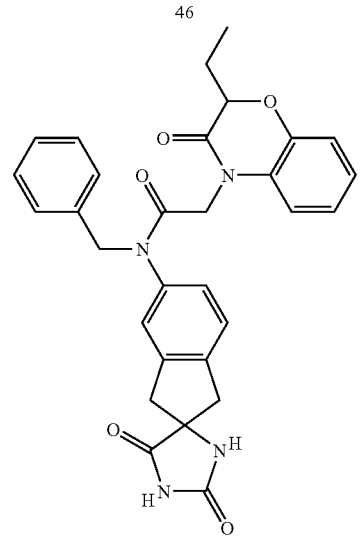
47
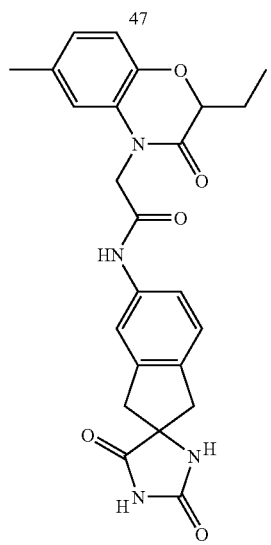

TABLE 2-continued
48
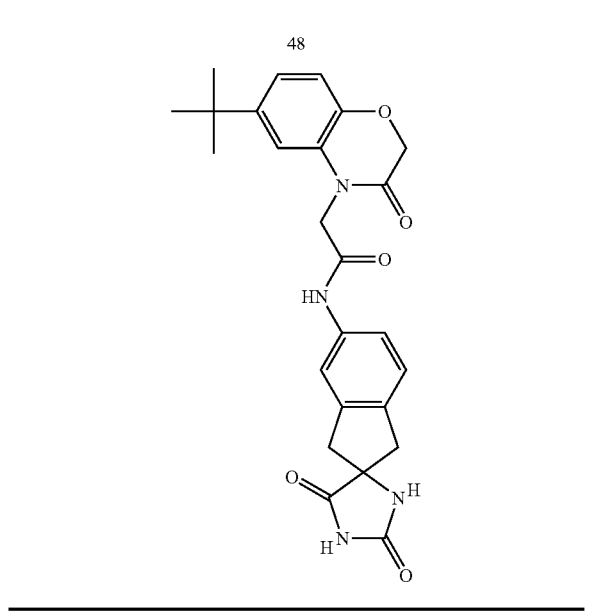
TABLE 3
49
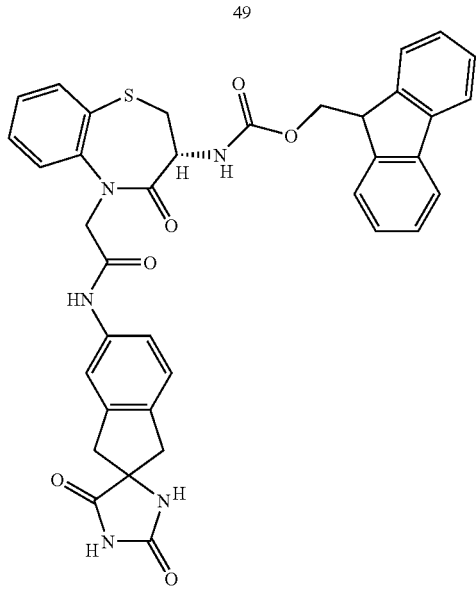
TABLE 3-continued
50
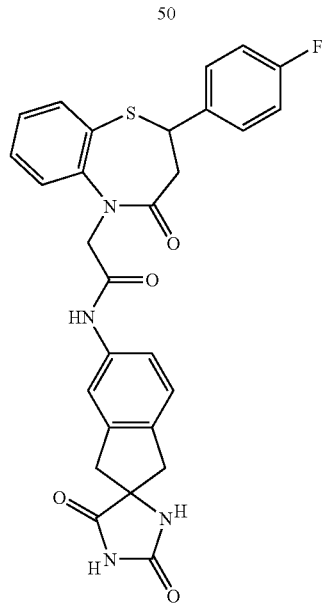
51
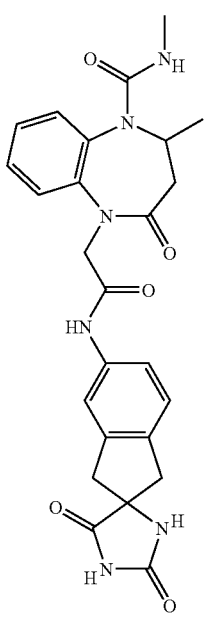

TABLE 3-continued
52
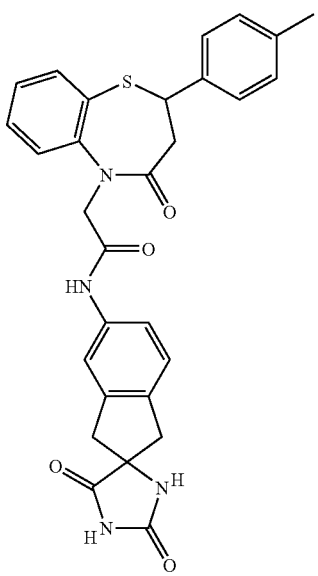
53
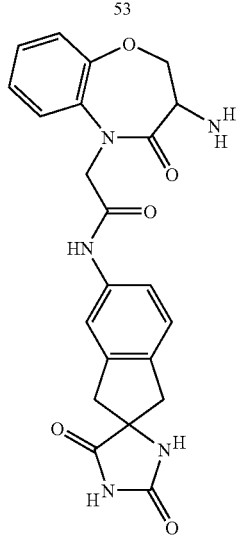
TABLE 3-continued
54
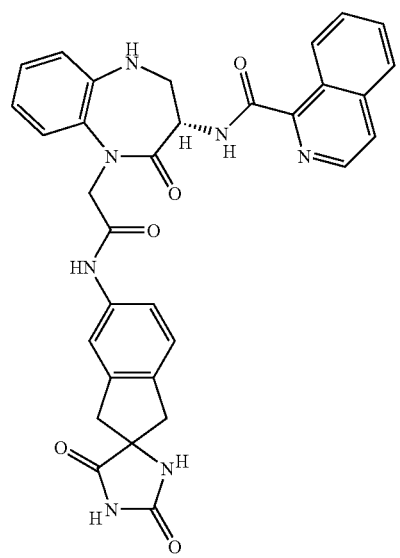
55
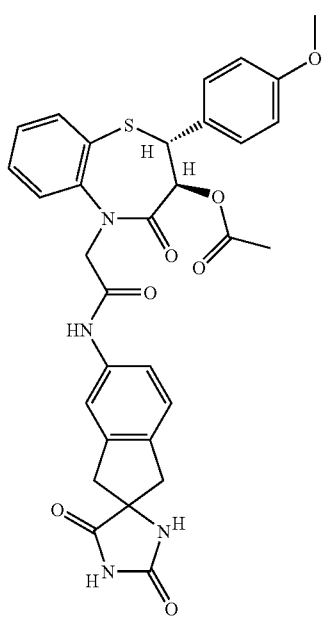

TABLE 3-continued
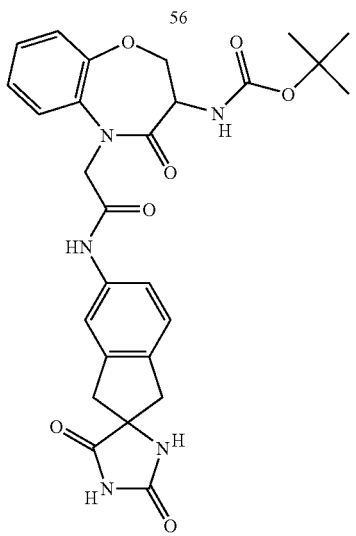
56
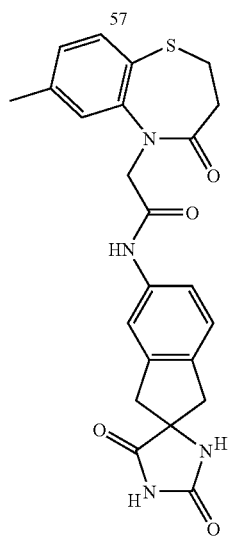
57
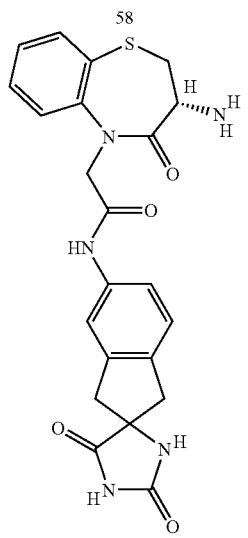
58
TABLE 3-continued
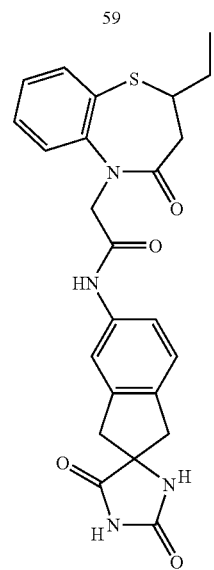
59
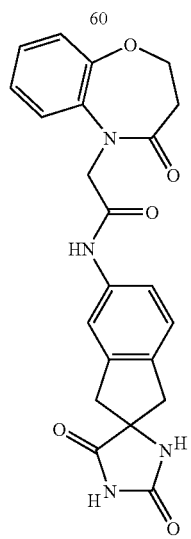
60
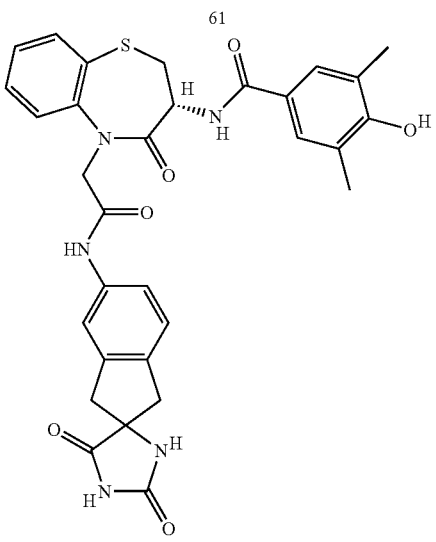
61

TABLE 3-continued
62
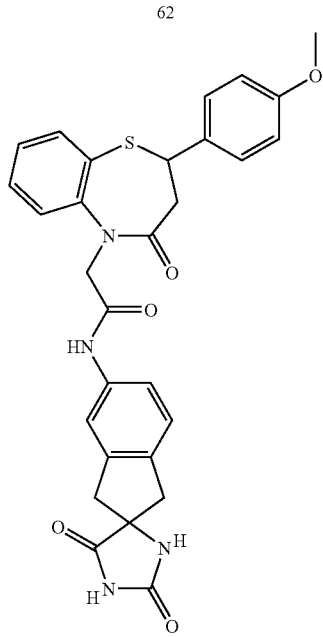
63
64
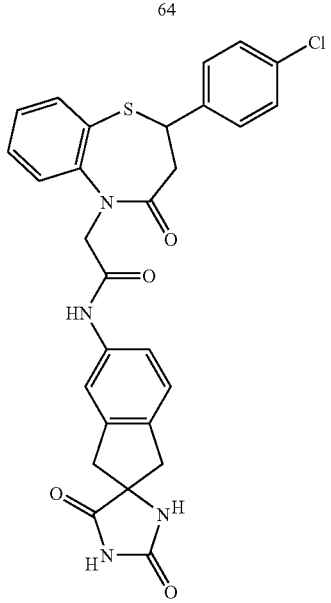
65
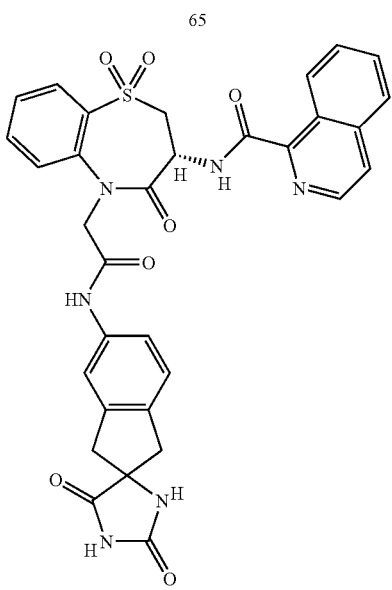

TABLE 3-continued
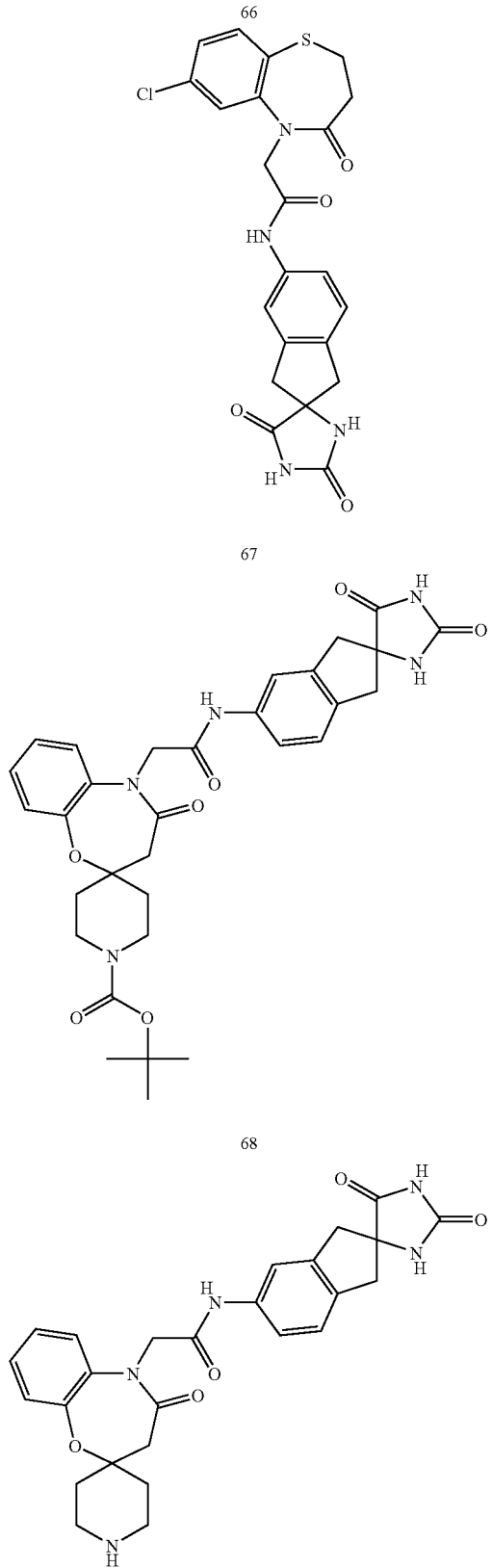

TABLE 3-continued
71
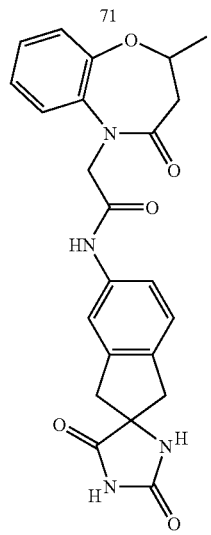
TABLE 4
72
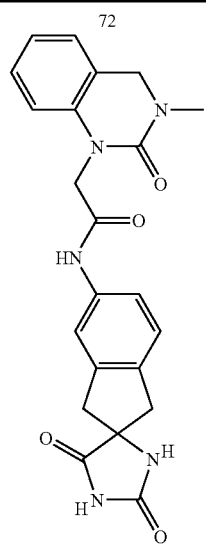
73
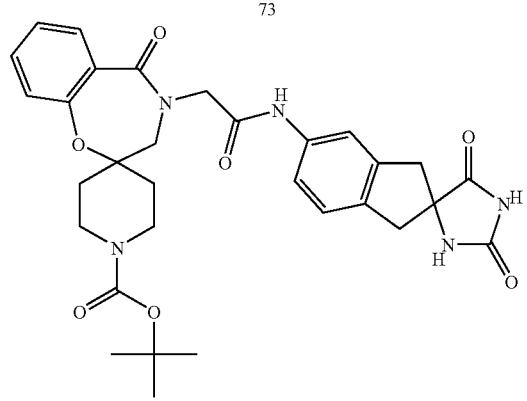
TABLE 4-continued
74
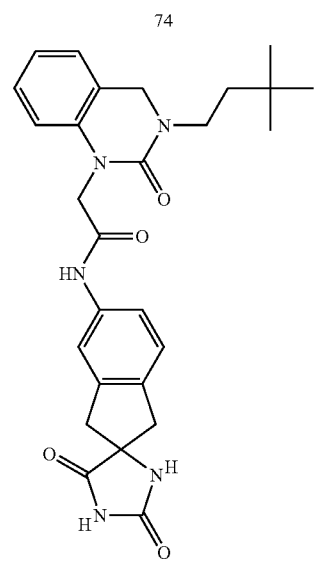
75
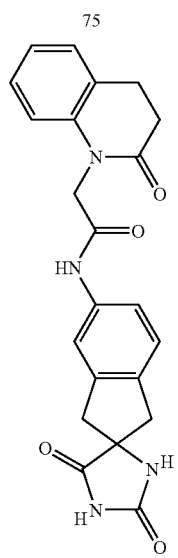

TABLE 4-continued

76

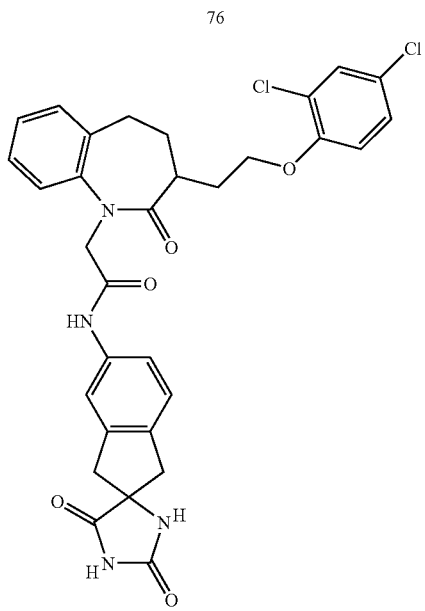

77

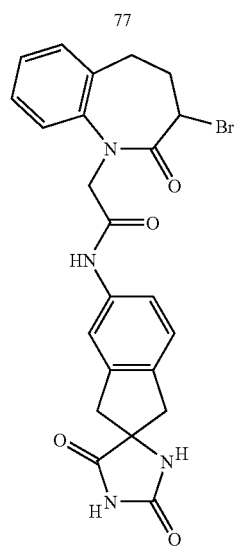

TABLE 4-continued

78

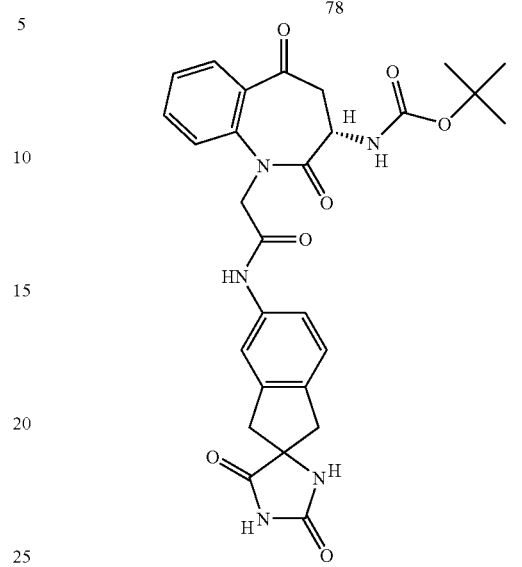

Compounds of the present invention may be readily prepared by methods well known in the art. Synthetic schemes for preparing the compounds of the present invention are shown below for illustrative purposes.

Scheme 1: Preparation of compounds of formula I:

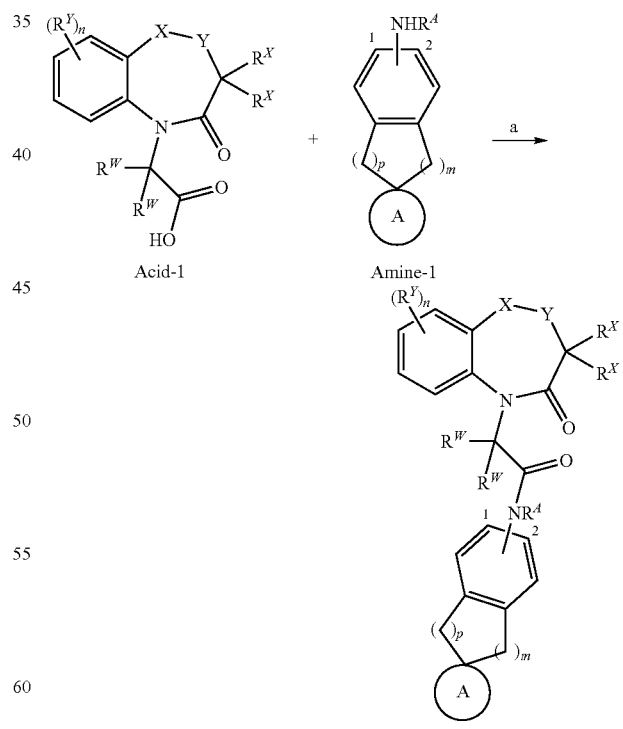

a) HATU, D$^i$PEA, DMF $R^Y$, n, X, Y, $R^X$, $R^W$, $R^A$, p, m and Ring A are as described above.

Compounds of formula I are prepared by adding Acid-1 to Amine-1 under conditions shown above in Scheme 1.

Scheme 1': Preparation of compounds of formulae I' (wherein Y is a bond) and I-A (wherein Y is a bond and $R^A$ is H):

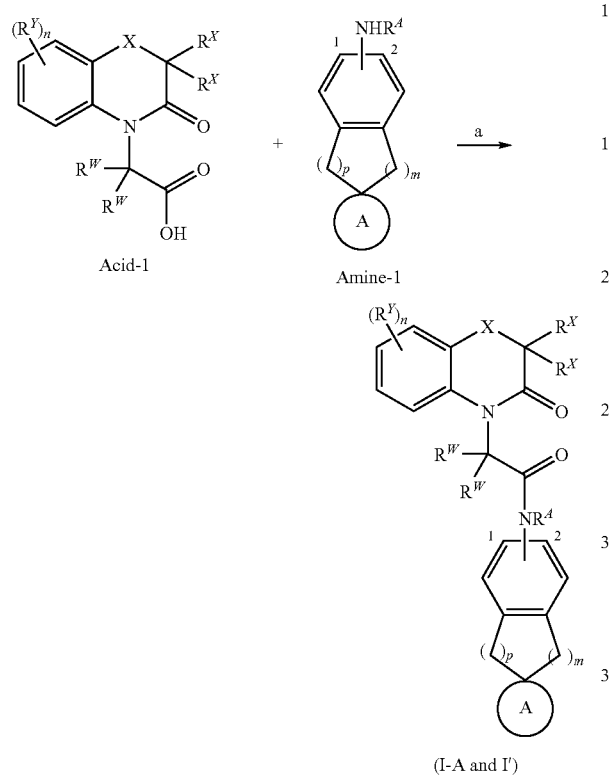

Acid-1  Amine-1

(I-A and I')

Compounds of formulae I-A or I' are prepared by adding Acid-1 to Amine-1 under conditions shown above in Scheme 1'.

Scheme 2: Preparation of Acid-1:

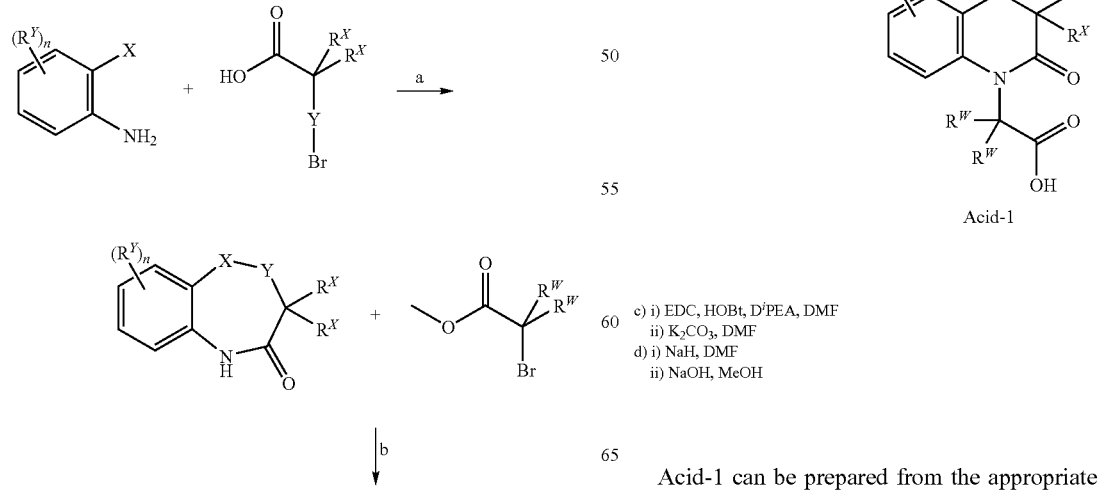

a) i) EDC, HOBt, D$^i$PEA, DMF
ii) K$_2$CO$_3$, DMF
b) i) NaH, DMF
ii) NaOH, MeOH

Acid-1 can be prepared from the appropriate substituted aniline and the bromo-acid, as shown in Scheme 2 above.

Scheme 2': Preparation of Acid-1 for compounds of formulae I-A and I' (wherein Y is a bond):

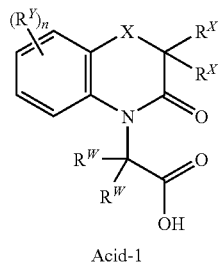

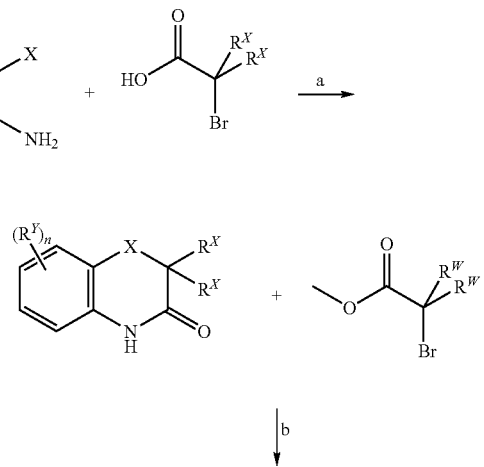

Acid-1 c) i) EDC, HOBt, D$^i$PEA, DMF
ii) K$_2$CO$_3$, DMF
d) i) NaH, DMF
ii) NaOH, MeOH

Acid-1 can be prepared from the appropriate substituted aniline and the bromo-acid, as shown in Scheme 2 above.

Scheme 3-A: Preparation of Amine-1:

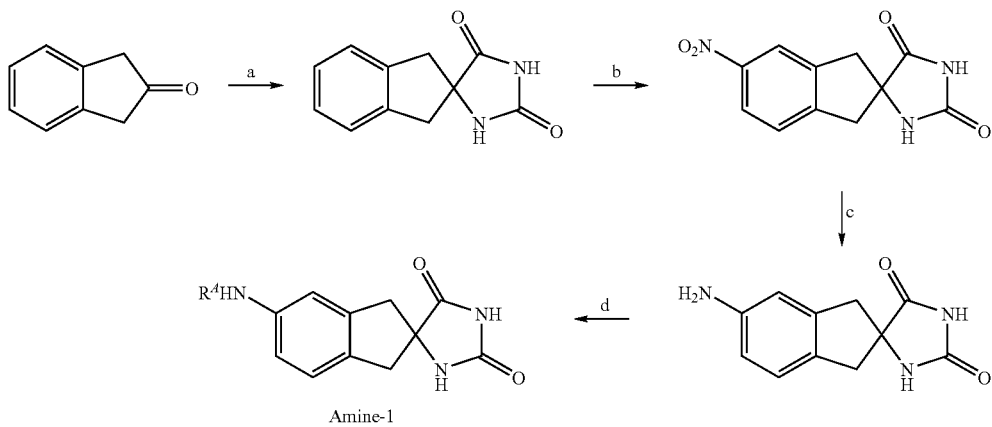

a) (NH$_4$)$_2$CO$_3$, NaCN, EtOH, H$_2$O
b) HNO$_3$
c) H$_2$, Pd/C, MeOH/EtOAc
d) Na(OAc)$_3$BH/DMF

Scheme 3-A: Preparation of Amine-1:

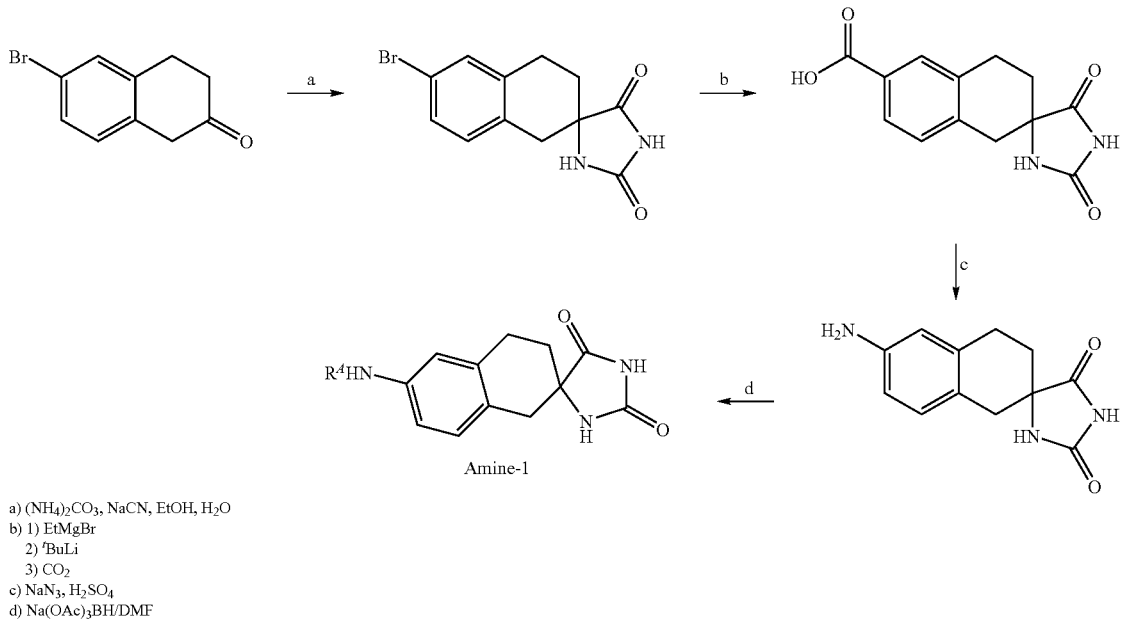

a) (NH$_4$)$_2$CO$_3$, NaCN, EtOH, H$_2$O
b) 1) EtMgBr
   2) $^t$BuLi
   3) CO$_2$
c) NaN$_3$, H$_2$SO$_4$
d) Na(OAc)$_3$BH/DMF

Scheme 3-A and Scheme 3-B illustrate the synthesis of Amine-1, wherein ring A in formula I is a hydantoin ring, and the bicyclic ring attached thereto is either an indane ring or a tetralin ring.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an active metabolite or residue thereof. As used herein, the term "active metabolite or residue thereof" means that a metabolite or residue thereof is also an antagonist of CGRP.

Pharmaceutically acceptable salts are well known in the art. For example, S. M. Berge, et al describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated". For example, exemplary additional therapeutic agents include, but are not limited to: nonopioid analgesics (indoles such as Etodolac, Indomethacin, Sulindac, Tolmetin; naphthylalkanones such sa Nabumetone; oxicams such as Piroxicam; para-aminophenol derivatives, such as Acetaminophen; propionic acids such as Fenoprofen, Flurbiprofen, Ibuprofen, Ketoprofen, Naproxen, Naproxen sodium, Oxaprozin; salicylates such as Asprin, Choline magnesium trisalicylate, Diflunisal; fenamates such as meclofenamic acid, Mefenamic acid; and pyrazoles such as Phenylbutazone); or opioid (narcotic) agonists (such as Codeine, Fentanyl, Hydromorphone, Levorphanol, Meperidine, Methadone, Morphine, Oxycodone, Oxymorphone, Propoxyphene, Buprenorphine, Butorphanol, Dezocine, Nalbuphine, and Pentazocine). Additionally, nondrug analgesic approaches may be utilized in conjunction with administration of one or more compounds of the invention. For example, anesthesiologic (intraspinal infusion, neural blocade), neuro-surgical (neurolysis of CNS pathways), neurostimulatory (transcutaneous electrical nerve stimulation, dorsal column stimulation), physiatric (physical therapy, orthotic devices, diathermy), or psychologic (cognitive methods-hypnosis, biofeedback, or behavioral methods) approaches may also be utilized. Additional appropriate therapeutic agents or approaches are described generally in The Merck Manual, Seventeenth Edition, Ed. Mark H. Beers and Robert Berkow, Merck Research Laboratories, 1999, and the Food and Drug Administration website, www.fda.gov, the entire contents of which are hereby incorporated by reference.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

The compounds of the present invention are useful in a method of antagonism of CGRP receptors in a patient such as a mammal in need of such antagonism comprising the administration of an effective amount of the compound. The present invention is directed to the use of the compounds disclosed herein as antagonists of CGRP receptors. In addition to primates, especially humans, a variety of other mammals can be treated according to the method of the present invention.

Another embodiment of the present invention is directed to a method for the treatment, control, amelioration, or reduction of risk of a disease or disorder in which the CGRP receptor is involved in a patient that comprises administering to the patient a therapeutically effective amount of a compound that is an antagonist of CGRP receptors.

The present invention is further directed to a method for the manufacture of a medicament for antagonism of CGRP receptors activity in humans and animals comprising combining a compound of the present invention with a pharmaceutical carrier or diluent.

The subject treated in the present methods is generally a mammal, for example a human being, male or female, in whom antagonism of CGRP receptor activity is desired. The term "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

The ability of the compounds of the present invention to act as CGRP antagonists makes them useful pharmacological agents for disorders that involve CGRP in humans and animals, but particularly in humans.

The compounds of the present invention have utility in treating, preventing, ameliorating, controlling or reducing the risk of one or more of the following conditions or diseases: headache; migraine; cluster headache; chronic tension type headache; pain; chronic pain; neurogenic inflammation and inflammatory pain; neuropathic pain; eye pain; tooth pain; diabetes; non-insulin dependent diabetes mellitus; vascular disorders; inflammation; arthritis; bronchial hyperreactivity, asthma; shock; sepsis; opiate withdrawal syndrome; morphine tolerance; hot flashes in men and women; allergic dermatitis; encephalitis; brain trauma; epilepsy; neurodegenerative diseases; skin diseases; neurogenic cutaneous redness, skin rosaceousness and erythema; tinnitus; inflammatory bowel disease, irritable bowel syndrome, cystitis; and other conditions that may be treated or prevented by antagonism of CGRP receptors. Of particular importance is the acute or prophylactic treatment of headache, including migraine and cluster headache.

The compounds of the present invention are further useful in a method for the prevention, treatment, control, amelioration, or reduction of risk of the diseases, disorders and conditions noted herein.

The compounds of the present invention are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with an anti-inflammatory or analgesic agent or an anti-migraine agent, such as an ergotamine or 5-HT.sub.1 agonists, especially a 5-HT.sub.1B/1D agonist, for example sumatriptan, naratriptan, zolmitriptan, eletriptan, almotriptan, frovatriptan, donitriptan, and rizatriptan; a cyclooxygenase inhibitor, such as a selective cyclooxygenase-2 inhibitor, for example rofecoxib, etoricoxib, celecoxib, valdecoxib or paracoxib; a non-steroidal anti-inflammatory agent or a cytokine-suppressing anti-inflammatory agent, for example with a compound such as aspirin, ibuprofen, ketoprofen, fenoprofen, naproxen, indomethacin, sulindac, meloxicam, piroxicam, tenoxicam, lomoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine and the like; or a steroidal analgesic. Similarly, the instant compounds may be administered with a pain reliever such as acetaminophen, phenacetin, codeine, fentanyl, sufentanil, methadone, acetyl methadol, buprenorphine or morphine.

Additionally, the present compounds may be used in conjunction with an interleukin inhibitor, such as an interleukin-1 inhibitor; an NK-1 receptor antagonist, for example aprepitant; an NMDA antagonist; an NR2B antagonist; a bradykinin-1 receptor antagonist; an adenosine A1 receptor agonist; a sodium channel blocker, for example lamotrigine; an opiate agonist such as levomethadyl acetate or methadyl acetate; a lipoxygenase inhibitor, such as an inhibitor of 5-lipoxygenase; an alpha receptor antagonist, for example indoramin; an alpha receptor agonist; a vanilloid receptor antagonist; an mGluR5 agonist, antagonist or potentiator; a GABA A receptor modulator, for example acamprosate calcium; nicotinic antagonists or agonists including nicotine; muscarinic agonists or antagonists; a selective serotonin reuptake inhibitor, for example fluoxetine, paroxetine, sertraline, duloxetine, escitalopram, or citalopram; a tricyclic antidepressant, for example amitriptyline, doxepin, protriptyline, desipramine, trimipramine, or imipramine; a leukotriene antagonist, for example montelukast or zafirlukast; an inhibitor of nitric oxide or an inhibitor of the synthesis of nitric oxide.

Also, the present compounds may be used in conjunction with ergot alkaloids, for example ergotamine, ergonovine, ergonovine, methylergonovine, metergoline, ergoloid mesylates, dihydroergotamine, dihydroergocornine, dihydroergocristine, dihydroergocryptine, dihydro-I-ergocryptine, dihydro-.theta.-ergocryptine, ergotoxine, ergocomine, ergocristine, ergocryptine, I-ergocryptine, .theta.-ergocryptine, ergosine, ergostane, bromocriptine, or methysergide.

Additionally, the present compounds may be used in conjunction with a beta-adrenergic antagonist such as timolol, propanolol, atenolol, or nadolol, and the like; a MAO inhibitor, for example phenelzine; a calcium channel blocker, for example flunarizine, nimodipine, lomerizine, verapamil, nifedipine, prochlorperazine or gabapentin; neuroleptics such as olanzapine and quetiapine; an anticonvulsant such as topiramate, zonisamide, tonabersat, carabersat or divalproex sodium; an angiotensin II antagonist, for example losartan and candesartan cilexetil; an angiotensin converting enzyme inhibitor such as lisinopril; or botulinum toxin type A.

The present compounds may be used in conjunction with a potentiator such as caffeine, an H2-antagonist, simethicone, aluminum or magnesium hydroxide; a decongestant such as phenylephrine, phenylpropanolamine, pseudoephedrine, oxymetazoline, epinephrine, naphazoline, xylometazoline, propylhexedrine, or levo-desoxy-ephedrine; an antitussive such as codeine, hydrocodone, caramiphen, carbetapentane, or dextromethorphan; a diuretic; a prokinetic agent such as metoclopramide or domperidone, and a sedating or non-sedating antihistamine.

In a particularly preferred embodiment the present compounds are used in conjunction with an anti-migraine agent, such as: an ergotamine; a 5-HT.sub.1 agonist, especially a 5-HT.sub.1B/1D agonist, in particular, sumatriptan, naratriptan, zolmitriptan, eletriptan, almotriptan, frovatriptan, donitriptan and rizatriptan; and a cyclooxygenase inhibitor, such as a selective cyclooxygenase-2 inhibitor, in particular, rofecoxib, etoricoxib, celecoxib, meloxicam, valdecoxib or paracoxib.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

In order that the invention described herein may be more fully understood, the following examples are set forth. It should be understood that these examples are for illustrative purposes only and are not to be construed as limiting this invention in any manner.

EXAMPLES

1',3'-Dihydrospiro[imidazolidine-4,2'-indene]-2,5-dione

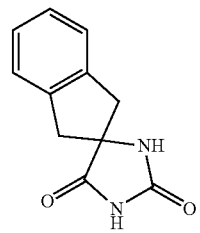

To a solution of 2-indanone (67.8 mmol, 9 g) and ammonium carbonate (684 mmol, 66 g) in ethanol (150 ml) and water (150 ml) was added NaCN (201.9 mmol, 9.9 g) and the reaction mixture was stirred at 70° C. for 3 h. The reaction mixture was cooled to 0° C. and the precipitated product was filtered, washed with water (4×) and desiccated. LC/MS (10% to 99%): M/Z (M+H)$^+$ (obs)=203; $t_R$=1.78.

5'-Nitro-1',3'-dihydrospiro[imidazolidine-4,2'-indene]-2,5-dione

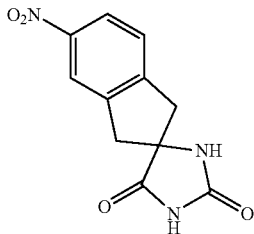

To a solution of conc. HNO₃ (30 ml) at 0° C. was added 1',3'-dihydrospiro[imidazolidine-4,2'-indene]-2,5-dione (3 g) in portions. The cooling bath was removed and the reaction mixture was stirred at room temperature for 1.5 h. The reaction mixture was poured into ice and the precipitated product was filtered, washed with water and desiccated. LC/MS (10% to 99%): M/Z (M+H)⁺ (obs)=248; $t_R$=1.82.

5'-Amino-1',3'-dihydrospiro[imidazolidine-4,2'-indene]-2,5-dione

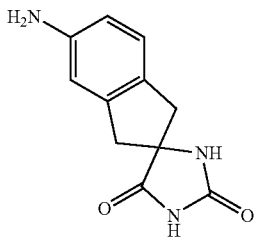

5'-Nitro-1',3'-dihydrospiro[imidazolidine-4,2'-indene]-2,5-dione (10.1 mmol, 2.5 g) and 10% Pd/C (0.25 g) in 1:1 EtOAc:MeOH (300 ml) were stirred under H₂ (1 atm) for 1.5 h. The solution was filtered and evaporated to give the title compound as a brown solid that was used with out further purification. LC/MS (10% to 99%): M/Z (M+H)⁺ (obs)=218; $t_R$=2.4.

2-Ethyl-2H-benzo[b][1,4]oxazin-3(4H)-one

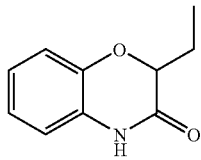

To a solution of 2-bromobutanoic acid (11 mmol, 2145 mg) in DMF (10 ml) was added EDC (12 mmol, 2.3 g) and HOBt (5 mmol, 675 mg) followed by the addition of 2-aminophenol (10 mmol, 1091 mg). The reaction mixture was stirred at room temperature for 2 h, diluted with water and extracted with ethyl acetate. The organic phase was washed with water, brine, dried over Na₂SO₄ and concentrated under reduced pressure. To the crude product in DMF (5 ml) was added K₂CO₃ (1.6 g) and the reaction mixture was stirred at room temperature overnight. The reaction mixture was diluted with water and extracted with EtOAc. The organic layer was washed with 1N HCl, Sat. NaHCO₃, dried over Na₂SO₄ and evaporated to dryness. Purification by column chromatography gave the desired product as a white solid. LC/MS (10% to 99%): M/Z (M+H)⁺ (obs)=178; $t_R$=2.36.

2-(2-Ethyl-3-oxo-2H-benzo[b][1,4]oxazin-4(3H)-yl) acetic Acid

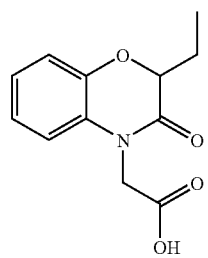

To a solution of 2-ethyl-2H-benzo[b][1,4]oxazin-3(4H)-one (1.5 mmol, 260 mg) in DMF (2 ml) was added NaH (1.8 mmol, 43 mg) and the reaction mixture was stirred at room temperature for 1 h before the dropwise addition of ethyl bromoacetate (1.5 mmol, 250 mg). The reaction mixture was stirred at room temperature overnight, diluted with water and extracted with ethyl acetate. The organic layer was washed with 1N HCl, Sat. NaHCO₃, dried over Na₂SO₄ and evaporated to dryness. The crude compound was dissolved in MeOH (3 ml) and 1 N NaOH (3 ml) and stirred for 2 h at room temperature. The MeOH was removed under reduced pressure and the resulting aqueous solution extracted with EtOAc. The aqueous layer was acidified to pH 2 with 1N HCl and extracted with EtOAc. The organic phase was dried over Na₂SO₄ and the solvent was evaporated to give the title compound. LC/MS (10% to 99%): M/Z (M+H)⁺ (obs)=236; $t_R$=2.4.

N-(2,5-Dioxo-1',3'-dihydrospiro[imidazolidine-4,2'-indene]-5'-yl)-2-(2-ethyl-3-oxo-2H-benzo[b][1,4]oxazin-4(3H)-yl)acetamide

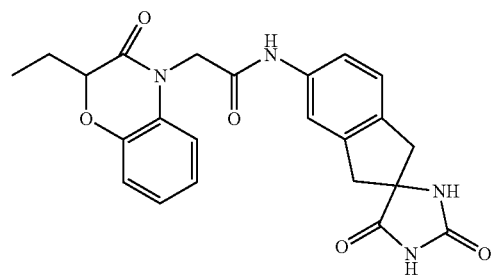

To a solution of 2-(2-ethyl-3-oxo-2H-benzo[b][1,4]oxazin-4(3H)-yl)acetic acid (0.2 mmol, 47 mg), 5'-amino-1',3'-dihydrospiro[imidazolidine-4,2'-indene]-2,5-dione (0.2 mmol, 43 mg) and D$^i$PEA (0.6 mmol, 104.5 μl) in DMF (1 ml) was added HATU (0.2 mmol, 76 mg) and the reaction mixture was stirred at room temperature for 16 h. Purification by preparative reverse phase HPLC using 10%-99% CH₃CN (0.035% TFA)/H₂O (0.05% TFA) gave the title compound. LC/MS (10% to 99%): M/Z (M+H)⁺ (obs)=435.2; $t_R$=2.71. H NMR (400 MHz, CDCl₃) δ 9.39 (s, 1H), 7.68 (s, 1H), 7.48 (s, 1H), 7.24 (q, 1H), 7.03 (d, 1H), 6.87-6.92 (m, 4H), 4.65 (q, 2H), 4.41 (q, 1H), 3.34 (q, 2H), 3.00 (q, 2H), 1.78 (m, 2H), 0.94 (t, 3H).

2-Butyl-2H-benzo[b][1,4]thiazin-3(4H)-one

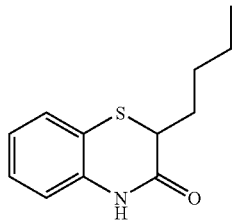

To a solution of 2-bromohexanoic acid (10 mmol, 1951 mg) in DMF (10 ml) was added 2-aminothiophenol (10 mmol, 1252 mg) and $K_2CO_3$ (50 mmol, 9.9 g) and the reaction mixture stirred at room temperature for 1 h. EDC (10 mmol, 1917 mg) and HOBt (10 mmol, 1351 mg) were added and the reaction mixture was stirred at room temperature for a further 1.5 h. The reaction mixture was diluted with 1N HCl and extracted with ethyl acetate. The organic phase was washed with sat. $NaHCO_3$, brine, dried over $Na_2SO_4$ and then filtered through a short plug of silica gel. Evaporation of the solvent gave product as a yellow solid that was used without further purification. LC/MS (10% to 99%): M/Z (M+H)$^+$ (obs)=222.0; $t_R$=3.07.

2-(2-Butyl-3-oxo-2H-benzo[b][1,4]thiazin-4(3H)-yl) acetic Acid

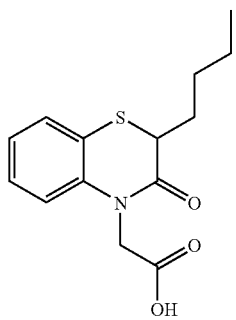

To a solution of 2-butyl-2H-benzo[b][1,4]thiazin-3(4H)-one (6.3 mmol, 1400 mg) in DMF (5 ml) was added NaH (6.9 mmol, 167 mg) and the reaction mixture was stirred at room temperature for 1 h before the dropwise addition of ethyl bromoacetate (6.3 mmol, 1052 mg). The reaction mixture was stirred at room temperature overnight, diluted with water and extracted with ethyl acetate. The organic layer was washed with 1N HCl, Sat. $NaHCO_3$, dried over $Na_2SO_4$ and evaporated to dryness. The crude compound was dissolved in MeOH (10 ml) and 1 N NaOH (10 ml) and stirred at room temperature for 2 h. The MeOH was removed under reduced pressure and the resulting aqueous solution extracted with EtOAc. The aqueous layer was acidified to pH 2 with 1N HCl and extracted with EtOAc. The organic phase was dried over $Na_2SO_4$ and the solvent was evaporated to give the title compound. LC/MS (10% to 99%): M/Z (M+H)$^+$ (obs)=280.2; $t_R$=3.01.

2-(2-Butyl-3-oxo-2H-benzo[b][1,4]thiazin-4(3H)-yl)-N-(2,5-dioxo-1',3'-dihydrospiro[imidazolidine-4,2'-indene]-5'-yl)acetamide

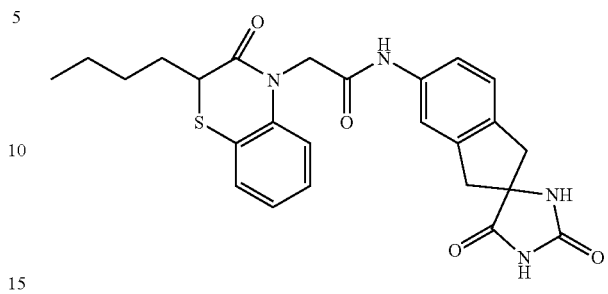

To a solution of 2-(2-butyl-3-oxo-2H-benzo[b][1,4]thiazin-4(3H)-yl)acetic acid (0.2 mmol, 56 mg), 5'-amino-1',3'-dihydrospiro[imidazolidine-4,2'-indene]-2,5-dione (0.2 mmol, 43 mg) and DIPEA (0.6 mmol, 104.5 µl) in DMF (1 ml) was added HATU (0.2 mmol, 76 mg) and the reaction mixture was stirred at room temperature for 16 h. Purification by preparative reverse phase HPLC using 10%-99% $CH_3CN$ (0.035% TFA)/$H_2O$ (0.05% TFA) gave the title compound. LC/MS (10% to 99%): M/Z (M+H)$^+$ (obs)=479.2; $t_R$=3.18. H NMR (400 MHz, $CDCl_3$) δ 8.19 (s, 1H), 7.55 (d, 1H), 7.42 (q, 1H), 7.25-7.33 (m, 2H), 7.16 (d, 1H), 7.07-7.15 (m, 2H), 4.86 (d, 1H), 4.60 (d, 1H), 3.59 (t, 1H), 3.27-3.34 (m, 2H), 2.97-3.04 (m, 2H), 1.6 (m, 1H), 1.24-1.28 (m, 5H), 0.83 (t, 3H).

Analytical data for certain compounds of the present invention are shown below in Table 5.

| Cmpd. # | LC/MS M + 1 | LC/RT min |
| --- | --- | --- |
| 1 | 435.5 | 1.36 |
| 2 | 476.4 | 1.54 |
| 3 | 483 | 1.52 |
| 4 | 491.4 | 1.73 |
| 5 | 435 | 2.71 |
| 6 | 464 | 3.09 |
| 7 | 457.2 | 1.11 |
| 8 | 467.4 | 0.93 |
| 9 | 448.4 | 1.33 |
| 10 | 441.2 | 1.18 |
| 11 | 479 | 3.18 |
| 12 | 483.6 | 1.14 |
| 13 | 423 | 1.11 |
| 14 | 407.2 | 1 |
| 15 | 451.5 | 1.42 |
| 16 | 451.3 | 1.49 |
| 17 | 435.5 | 1.37 |
| 18 | 449.5 | 1.43 |
| 19 | 533.5 | 0.99 |
| 20 | 479.3 | 1.2 |
| 21 | 475.3 | 1.6 |
| 22 | 447 | 1.37 |
| 23 | 512 | 1.66 |
| 24 | 435.5 | 1.37 |
| 25 | 462 | 1.51 |
| 26 | 513.3 | 1.55 |
| 27 | 421.3 | 1.2 |
| 28 | 470 | 1.47 |
| 29 | 514 | 1.36 |
| 30 | 491 | 1.39 |
| 31 | 450 | 1.41 |
| 32 | 493.5 | 1.31 |
| 33 | 533.3 | 0.87 |
| 34 | 477 | 1.64 |
| 35 | 495 | 1.27 |
| 36 | 506.5 | 1.18 |
| 37 | 489.5 | 1.45 |
| 38 | 511.5 | 1.6 |
| 39 | 492.5 | 1.08 |

-continued

| Cmpd. # | LC/MS M + 1 | LC/RT min |
|---|---|---|
| 40 | 449.5 | 1.33 |
| 41 | 533.5 | 0.85 |
| 42 | 475.3 | 1.36 |
| 43 | 520.5 | 1.21 |
| 44 | 527 | 1.21 |
| 45 | 449.3 | 1.43 |
| 46 | 525.3 | 1.96 |
| 47 | 449.3 | 1.45 |
| 48 | 464 | 1.47 |
| 49 | 674.6 | 1.5 |
| 50 | 531.3 | 1.55 |
| 51 | 491.4 | 0.88 |
| 52 | 527.4 | 1.35 |
| 53 | 436.6 | 0.72 |
| 54 | 590.6 | 1.16 |
| 55 | 601.5 | 1.54 |
| 56 | 536.4 | 1.34 |
| 57 | 451.2 | 1.21 |
| 58 | 452.1 | 0.94 |
| 59 | 465.5 | 1.4 |
| 60 | 421.2 | 2.21 |
| 61 | 600.6 | 1.19 |
| 62 | 543.4 | 1.28 |
| 63 | 581.5 | 1.78 |
| 64 | 547.4 | 1.61 |
| 65 | 639.4 | 1.2 |
| 66 | 471.2 | 1.25 |
| 67 | 590 | 1.56 |
| 68 | 490.5 | 0.81 |
| 69 | 513.2 | 1.45 |
| 70 | 519.3 | 1.44 |
| 71 | 435.4 | 1.09 |
| 72 | 420 | 1.06 |
| 73 | 590.7 | 1.5 |
| 74 | 490.4 | 1.67 |
| 75 | 405.3 | 1.02 |
| 76 | 608 | 1.96 |
| 77 | 497.3 | 1.34 |
| 78 | 548.9 | 1.34 |

Measuring CGRP Functional Antagonism Using SK-N-MC-BLA (4C10):

CGRP functional antagonism was characterized in a cell based transcriptional assay using a recombinant SK-N-MC line. To introduce the transcriptional reporter system, SK-N-MC cell line was transduced with a retroviral vector containing β-lactamase gene downstream of cAMP responsive promoter. The expression of β-lactamase is triggered by cAMP increase that is a downstream event of activation of endogenous CGRP receptor. Single clones were separated using Fluorescent Activated Cell Sorting (FACS) based on CGRP induced β-lactamase activity. β-lactamase activity was measured using a fluorescence energy transfer (FRET) dye, CCF4. CCF4 is a substrate of β-lactamase (Zlokarnik G, et al., Science, 279 (5347): 84-88, 1998) and cleaved into a product with different fluorescent signal from that of the parent. 4C10 clone was selected for dose dependent β-lactamase expression to different concentrations of CGRP and consistent pharmacology with previously published values. To evaluate functional antagonist activity of compounds in SK-N-MC (4C10) line, compounds were evaluated for their inhibition of β-lactamase expression in the presence of CGRP.

SK-N-MC (4C10) was cultured in Minimal Essential Media (MEM) (Invitrogen) supplemented with 1 mM non-essential amino acids solution (Invitrogen), 100 units/ml Penicillin-Streptomycin (Invitrogen), 1 mM sodium pyruvate (Invitrogen) and 10% fetal bovine serum. For the β-lactamase assay, low serum, 1% FBS in MEM was used. 30,000 cells were plated into each wells of poly-D-lysine coated 384-well plate (Becton Dickinson) a day prior to the assay. SK-N-MC (4C10) was preincubated with compounds for 30 min before the addition of 200 pM CGRP. The assay was incubated for 3 hours at 37° C. to allow β-lactamase expression. CCF4 dye was added and incubated for 2 hours at room temperature. The fluorescent signals were read using a fluorescence plate reader, Topology Compensatory Plate Reader (tcPR) at excitation wavelength, 400 nm and emission wavelengths, 460 nm for the product and 535 nm for the parent. The ratio of values at 460 to 535 nm was used to calculate percent of activation. Curve fitting and IC50 calculation were carried about using MOD3.

$I^{125}$-CGRP Binding Displacement Assay to Calculate $K_i$ of Compounds.

Purified SK-N-MC membrane was purchased from Perkin Elmer. The membrane was thawed quickly and placed on ice. The compounds were diluted with CGRP binding solution (25 mM Tris-HCl, pH7.4, 5 mM $MgCl_2$, 0.1% BSA and 0.05% Tween). The membrane was diluted 1:20 with the binding solution and homogenized with Tissue Matster-50 Homogenizer (Omni International) for 30 sec. The homogenized membrane was added to compounds in the binding solution. After 10 minutes incubation at room temperature, the final concentration of 46 pM, I125-iodotyrosyl-Calcitonin-Gene-Related Peptide (GE healthcare) was added to the membrane and compounds. After 2 hour incubation at room temperature, the reaction was stopped by rapid filtration through 0.5% PEI treated GF/C filter plate (Perkin Elmer) and the filter plate was washed with ice-cold washing solution (50 mM Tris HCl, pH7.4, 5 mM MgCl2 and 0.1% BSA) using cell harvester (Tomtec). The radioactivity of the filter plates were read on Topcount (Packard). The nonspecific binding was determined in the control reaction where 1 uM unlabelled CGRP was pre-incubated with the membrane prior to I125-CGRP addition. The total binding was determined in the control reaction of the membrane and I125-CGRP in the absence of compound. The percent displacement of I125-CGRP with compounds was calculated using nonspecific and total binding controls. The curve fitting was carried out using MOD3. Ki of compound was calculated by the equation of Cheng and Prusoff (Cheng Y., Prusoff W. H., Biochem. Pharmacol. 22: 3099-3108, 1973) using Kd of CGRP for the membrane and the amount of I125-CGRP used for the assay.

The exemplary compounds of the present invention in Tables 1-4 were found to be antagonists of CGRP in the $I^{125}$-CGRP binding assay described above and in the CGRP functional antagonism assay described above.

What is claimed is:

1. A compound of formula I:

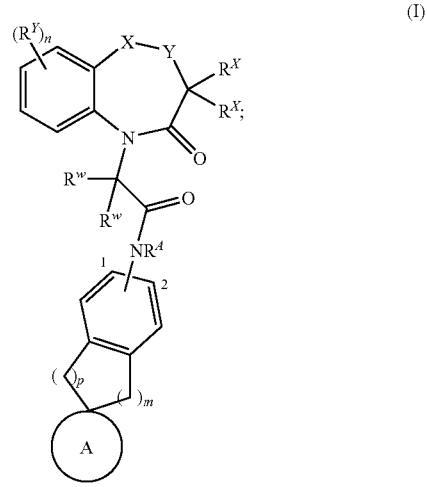

(I)

or a pharmaceutically acceptable salt thereof;

wherein:
said NR$^A$ group is attached to the phenyl ring at carbon atom 1 or 2;
X is O, NR$^A$, S, SO, or SO$_2$;
Y is a bond, C(R$^X$)$_2$, or —C(R$^X$)$_2$—C(R$^X$)$_2$—; or
wherein —X—Y— is —C(R$^X$)$_2$—C(R$^X$)$_2$—, —C(R$^X$)$_2$—C(R$^X$)$_2$—C(R$^X$)$_2$—, —C(R$^X$)$_2$—NR$^A$— or —C(R$^X$)$_2$—C(R$^X$)$_2$—NR$^A$—;
R$^A$ is hydrogen or C1-C6 aliphatic optionally substituted with up to 4 R$^1$ substituents;
ring A is a 4-7 membered heterocyclic ring having 1-4 heteroatoms selected from O, N, S, SO, or S(O)$_2$, wherein said heterocyclic ring is optionally fused to a phenyl or a 5-7 membered heterocyclic or heteroaryl ring having 1-4 heteroatoms selected from O, N, S, SO, or S(O)$_2$;
wherein ring A has at least one oxo substituent;
wherein ring A, together with the optionally fused ring, is optionally substituted with up to 5 R$^2$ substituents;
m is 1-3;
p is 1-3;
n is 1-4;
each R$^X$ is independently hydrogen, halo, aryl, heteroaryl, C1-C6 aliphatic, C1-C6 heteroaliphatic, aryl-C1-C6 aliphatic, aryl-C1-C6 heteroaliphatic, heteroaryl-C1-C6 aliphatic, heteroaryl-C1-C6 heteroaliphatic, or Q—R$^M$, wherein R$^X$ is optionally substituted with up to 5 R$^3$ substituents; or
two R$^X$, taken together with the carbon atom that they are attached to, form a 3-9 membered cycloaliphatic or heterocyclic ring, wherein said heterocyclic ring has up to 3 heteroatoms selected from O, S, and N; wherein said ring is optionally substituted with up to 3 R$^3$ substituents;
each R$^W$ is independently hydrogen, halo, aryl, heteroaryl, C1-C6 aliphatic, C1-C6 heteroaliphatic, aryl-C1-C6 aliphatic, heteroaryl-C1-C6 aliphatic, wherein R$^W$ is optionally substituted with up to 5 R$^4$ substituents; or
two R$^W$, taken together with the carbon atom that they are attached to, form a 3-9 membered cycloaliphatic or heterocyclic ring, wherein said heterocyclic ring has up to 3 heteroatoms selected from O, S, and N; wherein said ring is optionally substituted with up to 3 R$^4$ substituents;
wherein each occurrence of R$^1$, R$^2$, R$^3$, R$^4$, and R$^Y$ is independently Q—R$^M$;
wherein Q is a bond or is a C$_1$-C$_6$ aliphatic chain wherein up to two non-adjacent methylene units of Q are optionally replaced by CO, CO$_2$, COCO, CONR, OCONR, NRNR, NRNRCO, NRCO, NRCO$_2$, NRCONR, SO, SO$_2$, NRSO$_2$, SO$_2$NR, NRSO$_2$NR, O, S, or NR;
wherein each occurrence of R$^M$ is independently selected from R', halogen, NO$_2$, CN, OR', SR', N(R')$_2$, NR'C(O)R', NR'C(O)N(R')$_2$, NR'CO$_2$R', C(O)R', CO$_2$R', OC(O)R', C(O)N(R')$_2$, OC(O)N(R')$_2$, SOR', SO$_2$R', SO$_2$N(R')$_2$, NR'SO$_2$R', NR'SO$_2$N(R')$_2$, C(O)C(O)R', or C(O)CH$_2$C(O)R';
wherein each occurrence of R is independently selected from hydrogen or an optionally substituted C1-C6 aliphatic group or C1-C6 heteroaliphatic; and
wherein each occurrence of R' is independently selected from hydrogen or an optionally substituted group selected from C$_{1-8}$ aliphatic, C$_{6-10}$ aryl, a heteroaryl ring having 5-10 ring atoms, or a heterocyclyl ring having 3-10 ring atoms, or wherein R and R' taken together with the atom(s) to which they are bound, or two occurrences of R' taken together with the atom(s) to which they are bound, form a 3-8 membered cycloalkyl, heterocyclyl, aryl, or heteroaryl ring having 0-3 heteroatoms independently selected from nitrogen, oxygen, or sulfur.

2. The compound according to claim 1, wherein m is 1 and p is 1.
3. The compound according to claim 1, wherein X is O, NR$^A$, S, SO, or SO$_2$ and Y is a bond, C(R$^X$)$_2$, or —C(R$^X$)$_2$—C(R$^X$)$_2$—.
4. The compound according to claim 1, wherein X is O or S.
5. The compound according to claim 1, wherein Y is a bond.
6. The compound according to claim 1, wherein Y is C(R$^X$)$_2$.
7. The compound according to claim 1, wherein one R$^X$ is C1-C6 aliphatic optionally substituted with one or more halo, OH, C1-C4 alkoxy, C1-C4 alkoxy carbonyl, or di-(C1-C4 alkyl) amino.
8. The compound according to claim 1, wherein one R$^X$ is phenyl or heteroaryl optionally substituted with one or more substituents independently selected from C1-C6 aliphatic, cyano, halo, halo-C1-C6 aliphatic, aryl-C1-C6 aliphatic, heteroaryl-C1-C6 aliphatic, aralkyloxy, di(C1-C6 aliphatic) amino, O—C1-C6 aliphatic, S(O)—C1-C6 aliphatic, or S(O)$_2$—C1-C6 aliphatic.
9. The compound according to claim 1, wherein two R$^X$, taken together with the carbon atom that they are attached to, form an optionally substituted 3-9 membered cycloaliphatic or heterocyclic, monocyclic, bicyclic, or tricyclic ring.
10. The compound according to claim 1, wherein one R$^X$ is —C(O)NH—R$^M$, —NHC(O)—R$^M$, —NHC(O)O—R$^M$, wherein R$^M$ is an optionally substituted phenyl, heteroaryl or heterocyclic group.
11. The compound according to claim 1, wherein both R$^W$ are hydrogen.
12. The compound according to claim 1, wherein one R$^W$ is hydrogen and the other R$^W$ is C1-C6 aliphatic optionally substituted with one or more halo, OH, C1-C4 alkoxy, C1-C4 alkoxy carbonyl, or di-(C1-C4 alkyl) amino.
13. The compound according to claim 1, wherein R$^A$ is hydrogen.
14. The compound according to claim 1, wherein each Q is independently a bond or a C1-C6 aliphatic chain wherein up to two non-adjacent methylene units of Q are optionally replaced by CO, CO$_2$, CONR, OCONR, NRCO, NRCO$_2$, NRCONR, SO, SO$_2$, NRSO$_2$, SO$_2$NR, NRSO$_2$NR, O, S, or NR, wherein R is hydrogen or C1-C6 alkyl.
15. The compound according to claim 14, wherein each R$^M$ is independently R'.
16. The compound according to claim 1, wherein ring A is:

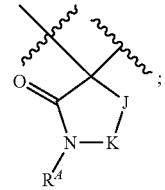

(a)

wherein:
J is selected from C(O), C(R$^5$)$_2$, =N—, —NR$^{6b}$, or =CR$^{6a}$;
K is selected from C(O), SO2, =N—, —NR$^{6b}$, =CR$^{6b}$, or C(R$^5$)$_2$;
each R$^5$ is independently hydrogen, C1-C6 aliphatic optionally substituted with up to 5 substituents selected from oxo, halo, —OH, —O—C1-C6 aliphatic, NH$_2$, NH(C1-C6 aliphatic), or N(C1-C6 aliphatic)$_2$;
each R$^{6a}$ and R$^{6b}$ is independently selected from hydrogen, halo, CN, —OH, —O—C1-C6 aliphatic, NH$_2$, NH(C1-

C6 aliphatic), or N(C1-C6 aliphatic)$_2$, C1-C6 aliphatic optionally substituted with up to 5 substituents selected from oxo, halo, —OH, —O—C1-C6 aliphatic, NH$_2$, NH(C1-C6 aliphatic), or N(C1-C6 aliphatic)$_2$, phenyl optionally substituted with up to 5 Q—R$^M$ substituents, or a 5-7 membered heterocycle or heteroaryl ring having up to 4 heteroatoms selected from O, N, S, SO, or SO2, wherein said heterocycle or heteroaryl ring is optionally substituted with up to 5 Q—R$^M$ substituents; or R$^{6a}$ and R$^{6b}$ and the atoms to which they are attached are joined to form a ring selected from cyclopentyl, cyclohexyl, cyclopentenyl, cyclohexenyl, phenyl, pyridyl, pyrimidinyl, pyrazinyl, pyridazinyl, furanyl, dihydrofuranyl, dihydropyranyl, thiazolyl, isothiazolyl, oxazolyl, isoxazolyl, imidazolyl, triazolyl, thienyl, dihyrothienyl, or dihydrothiopyranyl, wherein said ring is optionally substituted with up to 5 Q—R$^M$ substituents.

17. The compound according to claim 1, wherein said compound is of formulae I-A or I-B:

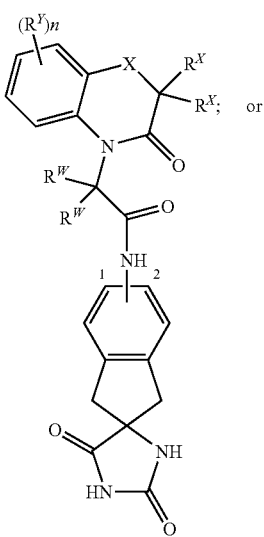

(I-A)

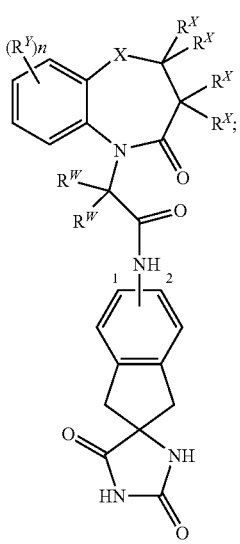

(I-B)

or a pharmaceutically acceptable salt thereof;

wherein:
the

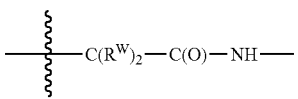

group is attached to the phenyl ring at carbon atom 1 or 2.

18. A compound of formula I':

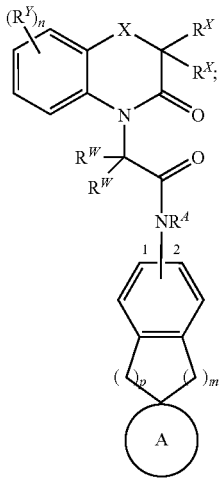

(I')

or a pharmaceutically acceptable salt thereof;
wherein:
said NR$^A$ group is attached to the phenyl ring at carbon atom 1 or 2;
X is O, NR$^A$, S, SO, or SO$_2$;
R$^A$ is hydrogen or C1-C6 aliphatic optionally substituted with up to 4 R$^1$ substituents;
ring A is a 4-7 membered heterocyclic ring having 1-4 heteroatoms selected from O, N, S, SO, or S(O)$_2$, wherein said heterocyclic ring is optionally fused to a phenyl or a 5-7 membered heterocyclic or heteroaryl ring having 1-4 heteroatoms selected from O, N, S, SO, or S(O)$_2$;
wherein ring A has at least one oxo substituent;
wherein ring A, together with the optionally fused ring, is optionally substituted with up to 5 R$^2$ substituents;
m is 1-3;
p is 1-3;
n is 1-4;
each R$^X$ is independently hydrogen, halo, aryl, heteroaryl, C1-C6 aliphatic, C1-C6 heteroaliphatic, aryl-C1-C6 aliphatic, aryl-C1-C6 heteroaliphatic, heteroaryl-C1-C6 aliphatic, heteroaryl-C1-C6 heteroaliphatic, wherein R$^X$ is optionally substituted with up to 5 R$^3$ substituents; or
two R$^X$, taken together with the carbon atom that they are attached to, form a 3-9 membered cycloaliphatic or heterocyclic ring, wherein said heterocyclic ring has up to 3 heteroatoms selected from O, S, and N; wherein said ring is optionally substituted with up to 3 R$^3$ substituents;
each R$^W$ is independently hydrogen, halo, aryl, heteroaryl, C1-C6 aliphatic, C1-C6 heteroaliphatic, aryl-C1-C6 aliphatic, heteroaryl-C1-C6 aliphatic, wherein R$^X$ is optionally substituted with up to 5 R$^4$ substituents; or
two R$^W$, taken together with the carbon atom that they are attached to, form a 3-9 membered cycloaliphatic or heterocyclic ring, wherein said heterocyclic ring has up to 3 heteroatoms selected from O, S, and N; wherein said ring is optionally substituted with up to 3 $R^4$ substituents;

wherein each occurrence of $R^1$, $R^2$, $R^3$, $R^4$, and $R^Y$ is independently $Q-R^M$;

wherein Q is a bond or is a $C_1-C_6$ aliphatic chain wherein up to two non-adjacent methylene units of Q are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR;

wherein each occurrence of $R^M$ is independently selected from R', halogen, $NO_2$, CN, OR', SR', $N(R')_2$, NR'C(O)R', $NR'C(O)N(R')_2$, $NR'CO_2R'$, C(O)R', $CO_2R'$, OC(O)R', $C(O)N(R')_2$, $OC(O)N(R')_2$, SOR', $SO_2R'$, $SO_2N(R')_2$, $NR'SO_2R'$, $NR'SO_2N(R')_2$, C(O)C(O)R', or C(O)CH$_2$C(O)R', wherein each occurrence of R is independently selected from hydrogen or an optionally substituted C1-C6 aliphatic group or C1-C6 heteroaliphatic;

wherein each occurrence of R' is independently selected from hydrogen or an optionally substituted group selected from $C_{1-8}$ aliphatic, $C_{6-10}$ aryl, a heteroaryl ring having 5-10 ring atoms, or a heterocyclyl ring having 3-10 ring atoms, or wherein R and R' taken together with the atom(s) to which they are bound, or two occurrences of R' taken together with the atom(s) to which they are bound, form a 3-8 membered cycloalkyl, heterocyclyl, aryl, or heteroaryl ring having 0-3 heteroatoms independently selected from nitrogen, oxygen, or sulfur.

19. A compound selected from:

1

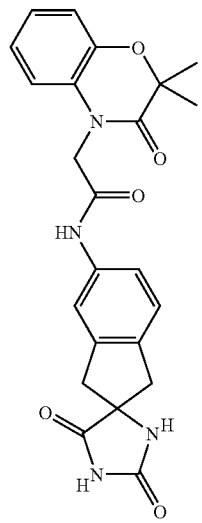

2

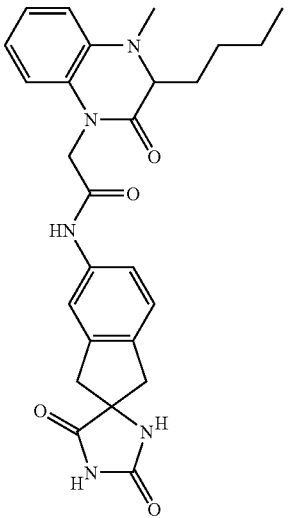

3

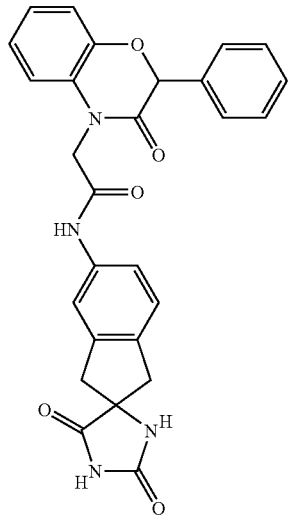

4

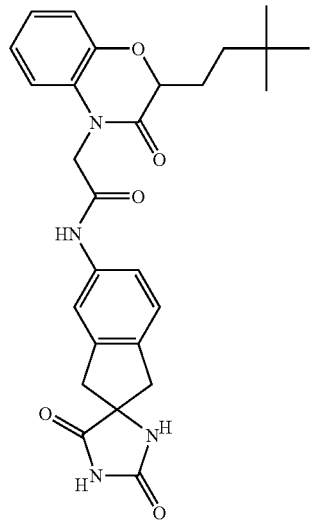

5
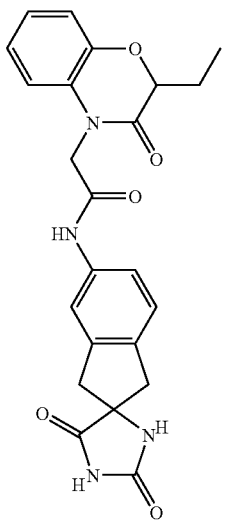
6
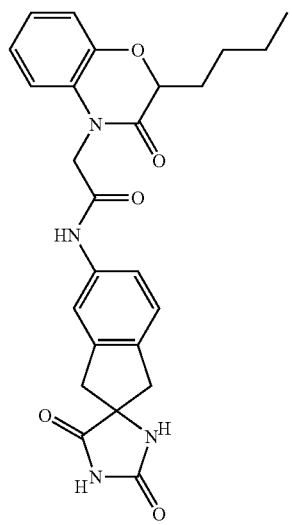
7
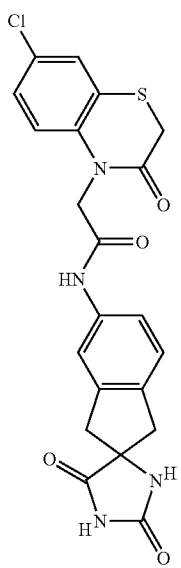
8
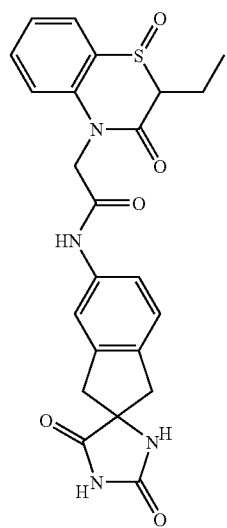

-continued
9
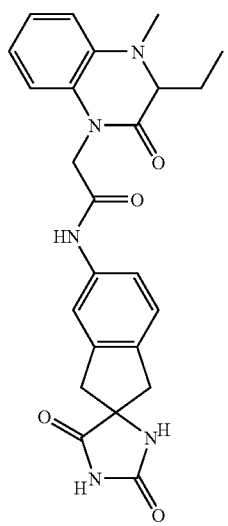
10
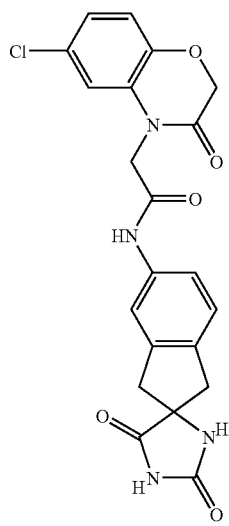
11
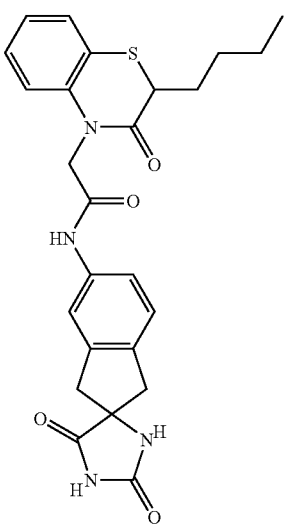
12
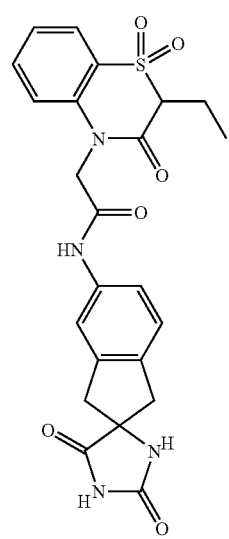

-continued
13
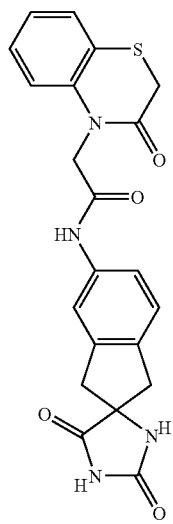
14
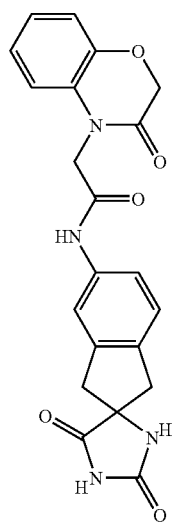
15
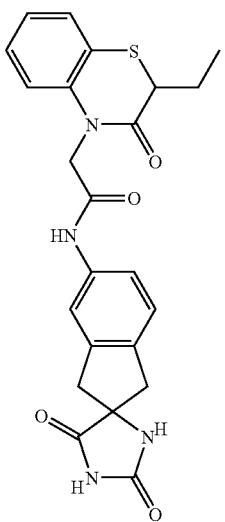
16
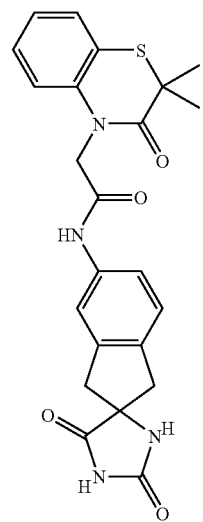

-continued
17
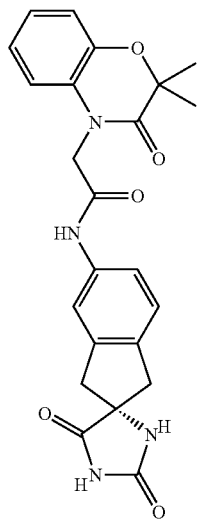
18
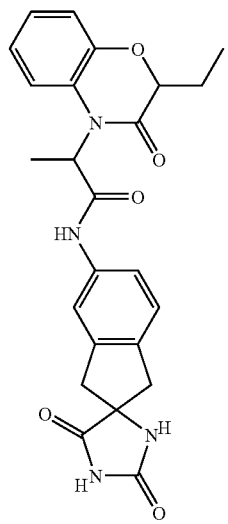
19
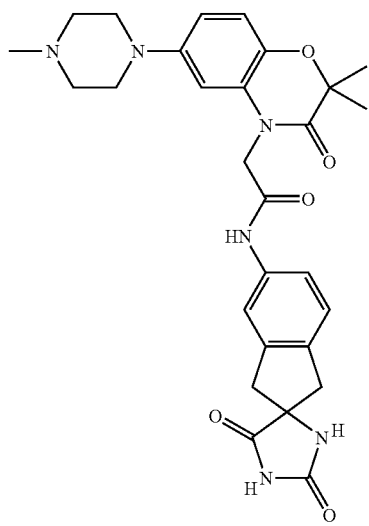
20
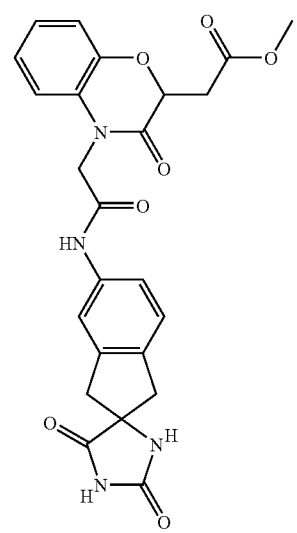

-continued
21
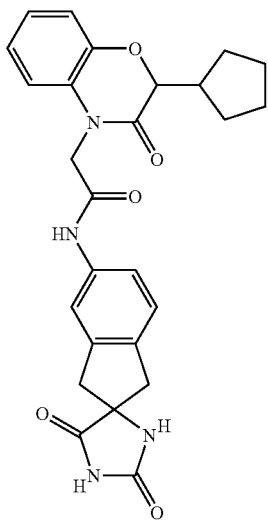
22
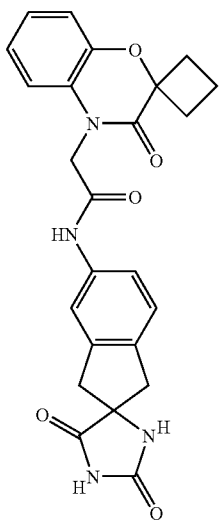
23
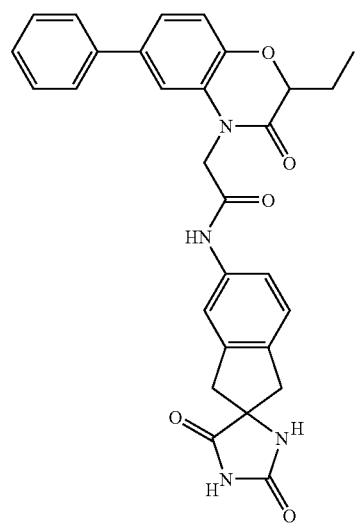
24
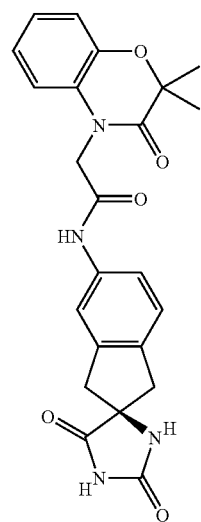

25
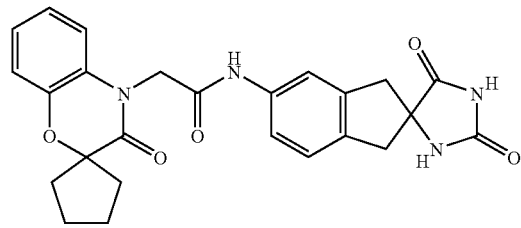
26
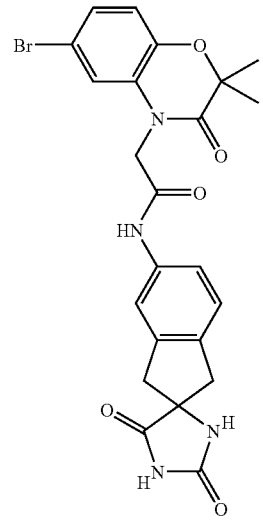
27
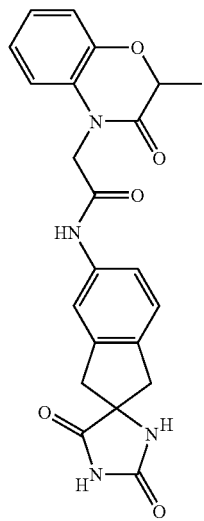
28
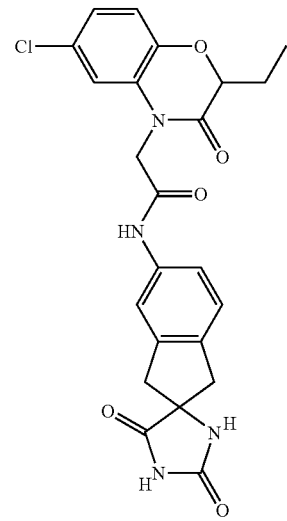

29
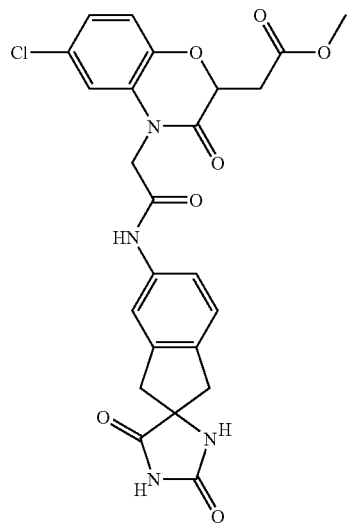
30
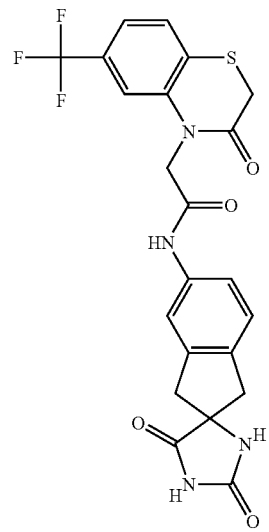
31
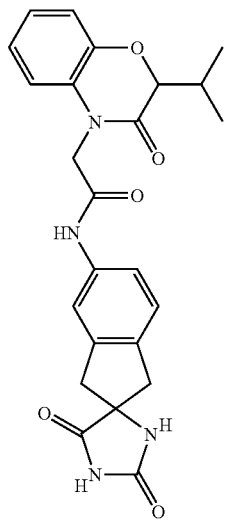
32
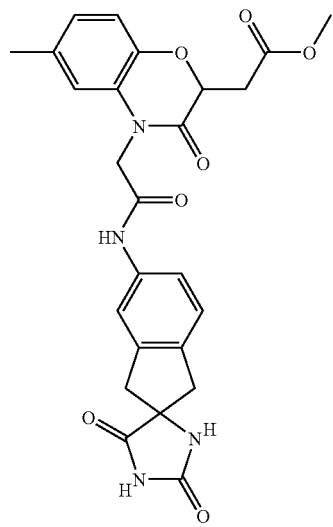

-continued
33
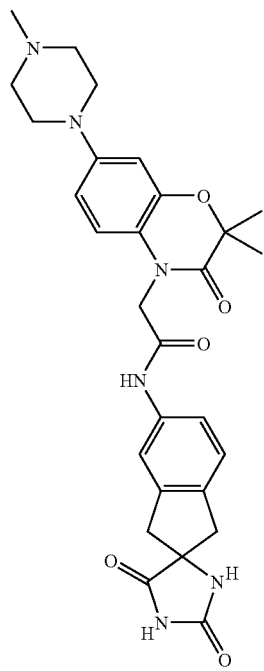
34
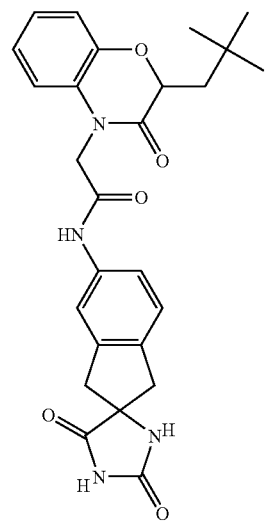
35
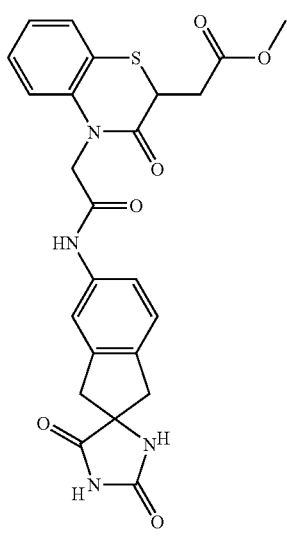
36
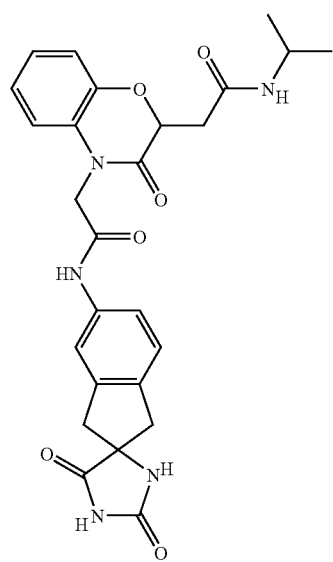

37
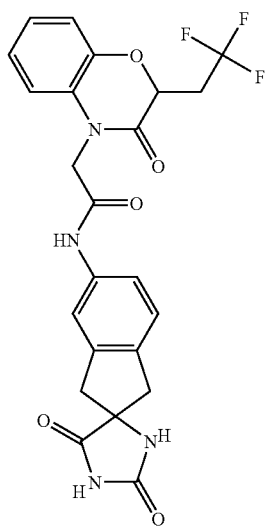
38
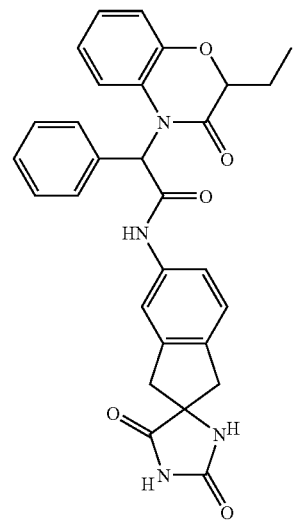
39
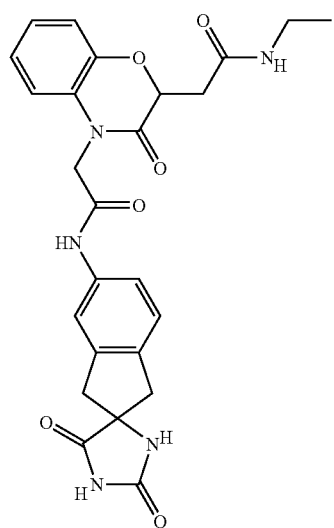
40
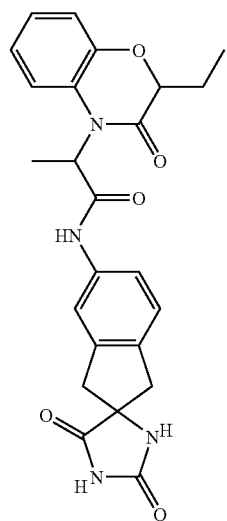

41
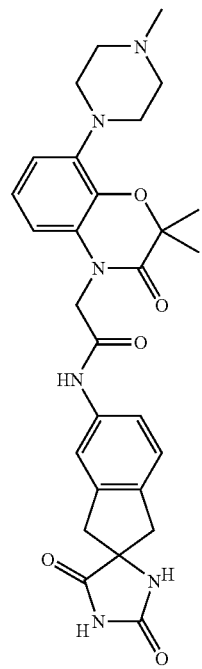
42
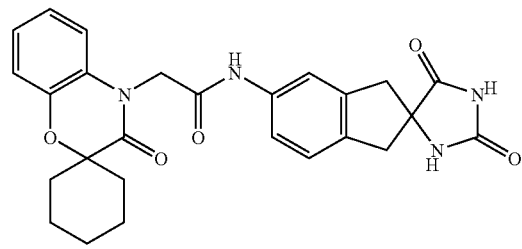
43
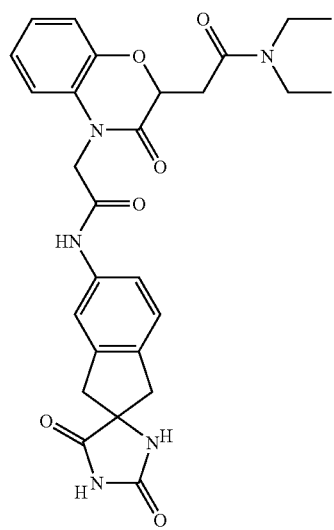
44
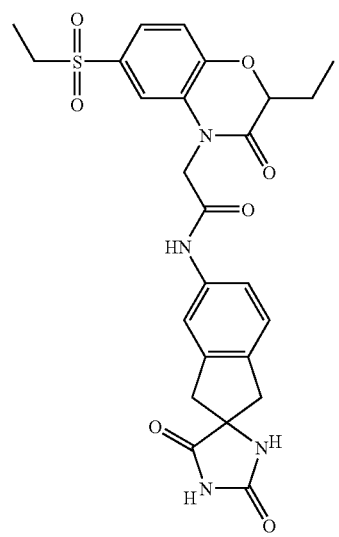

| 45 | 46 |
|---|---|
| 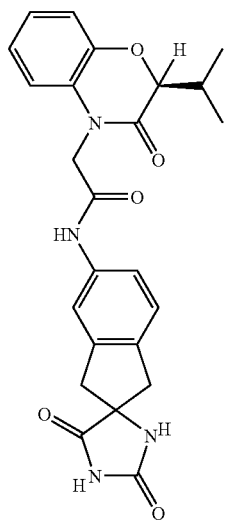 | 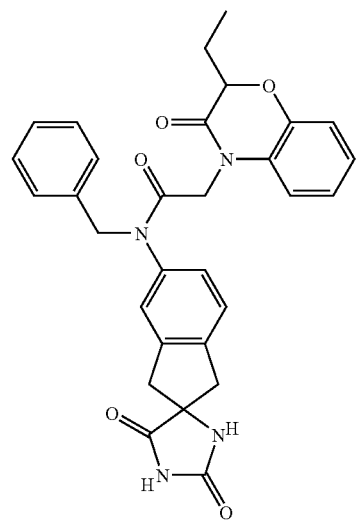 |
| 47 | 48 |
| 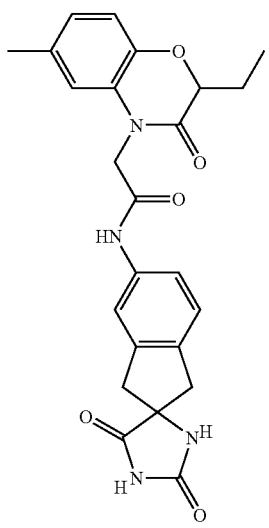 | 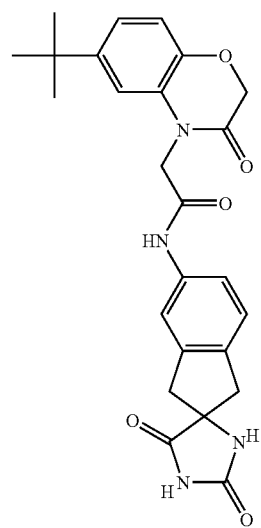 |

-continued
49
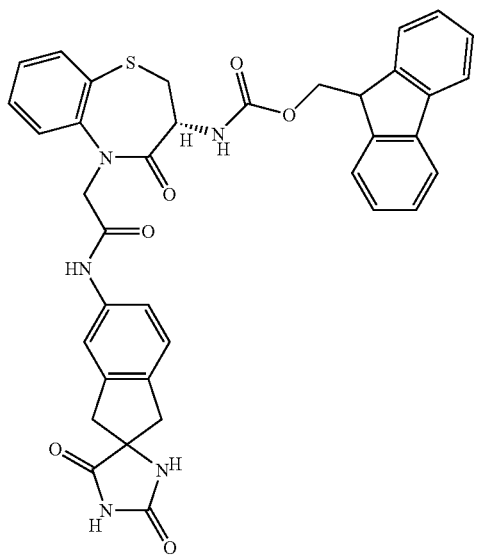
50
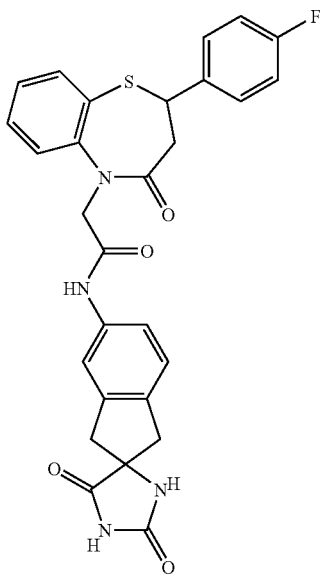
51
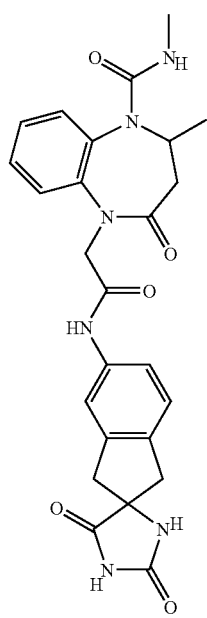
52
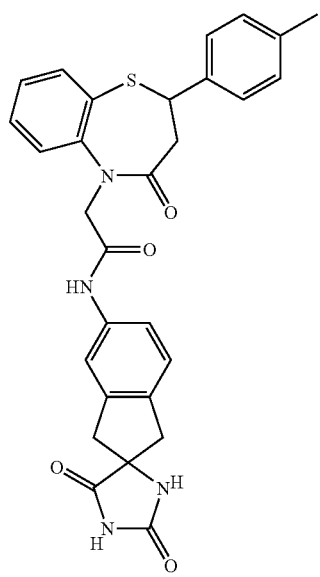

53
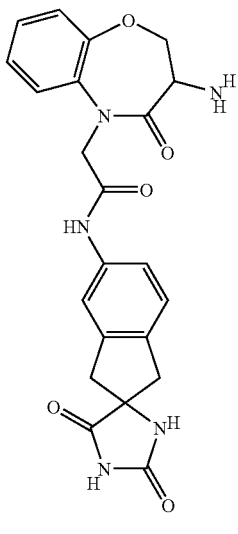
54
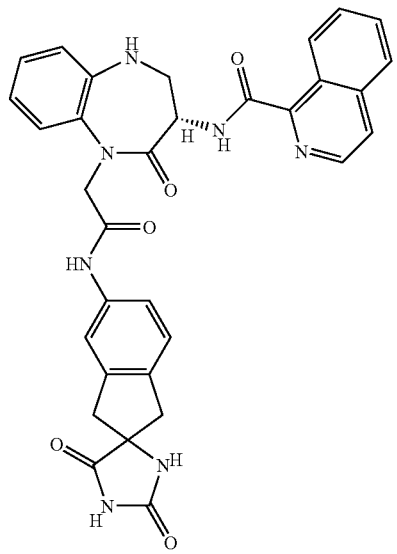
55
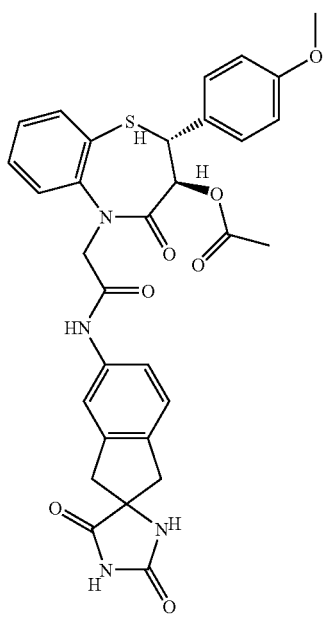
56
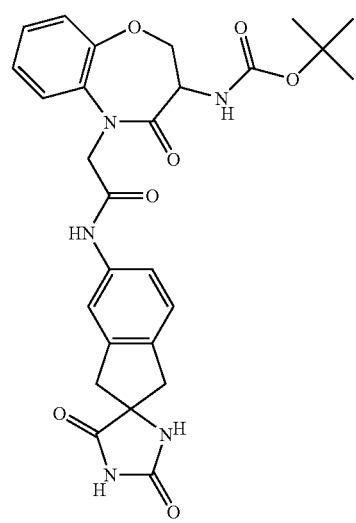

57
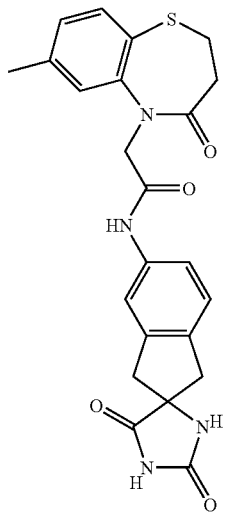
58
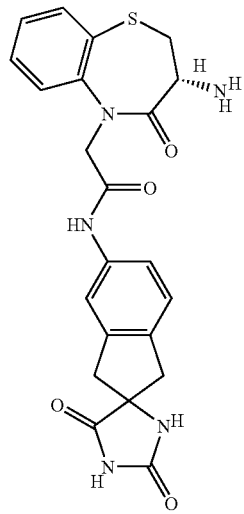
59
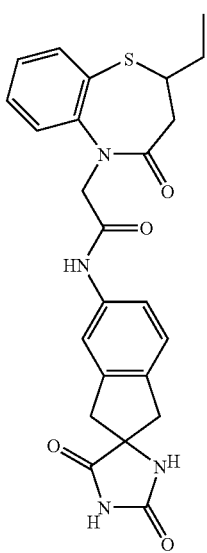
60
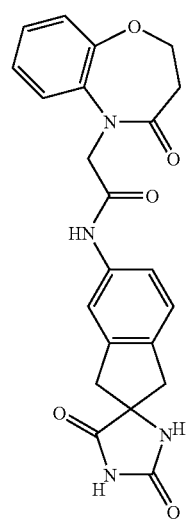

61
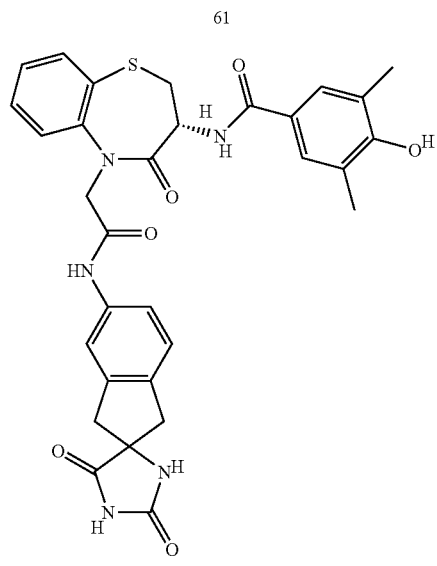
62
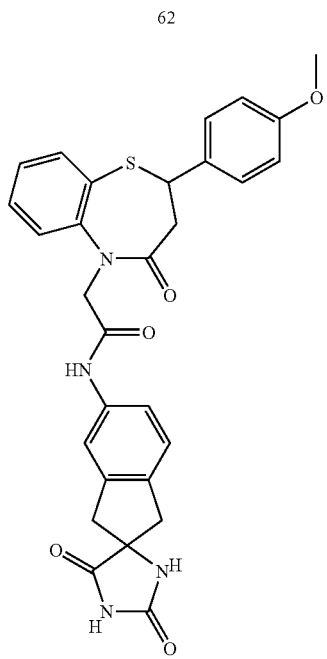
63
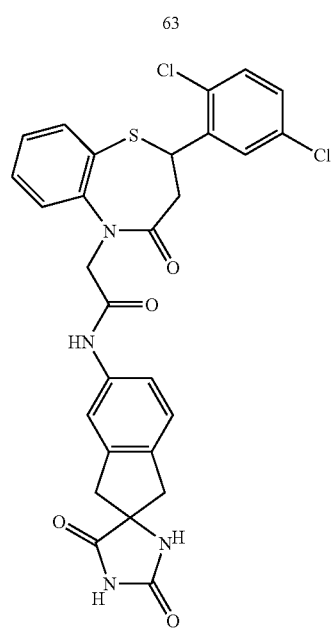
64
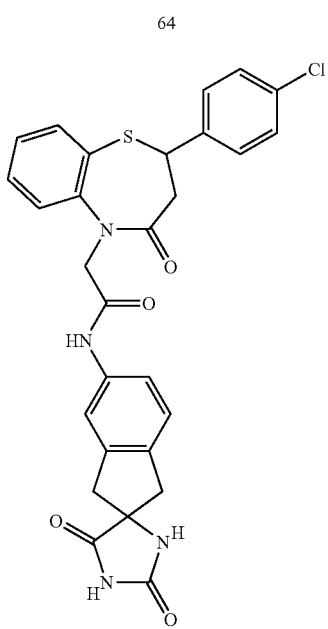

65
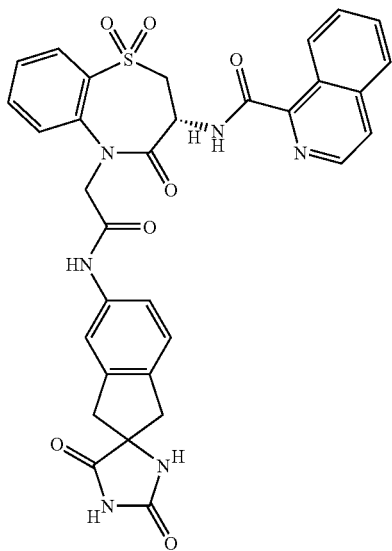
66
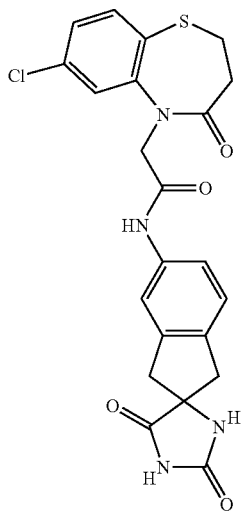
67
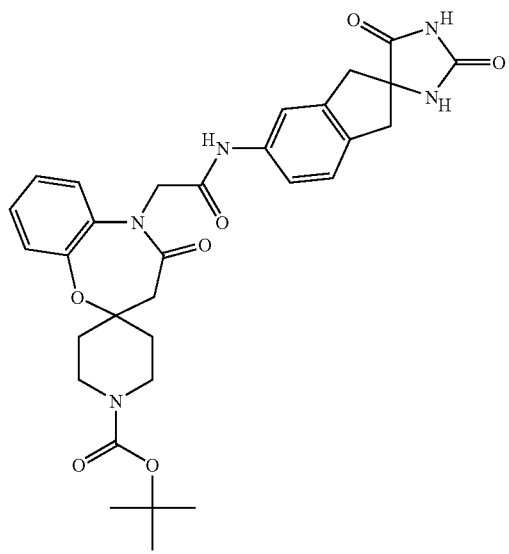
68
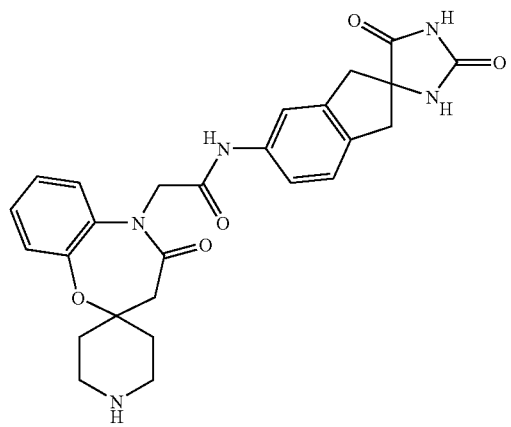

69
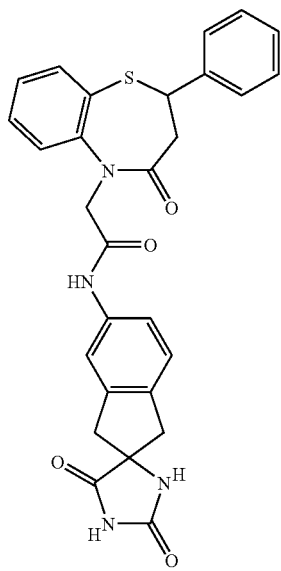
70
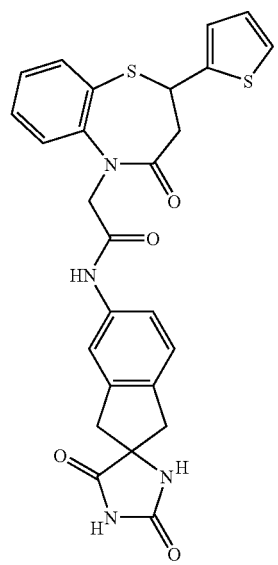
71
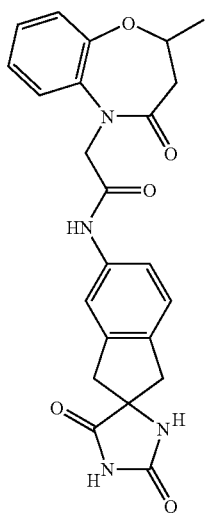
72
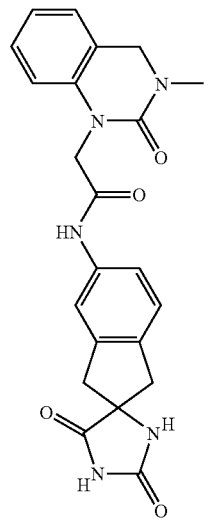

73
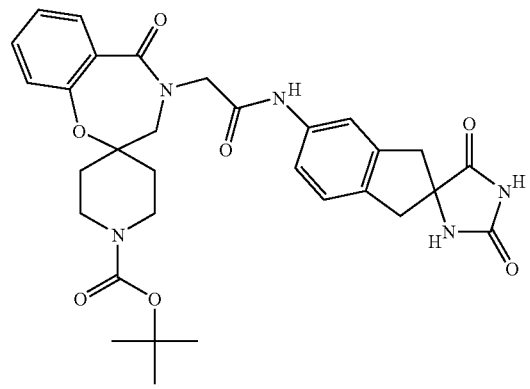
74
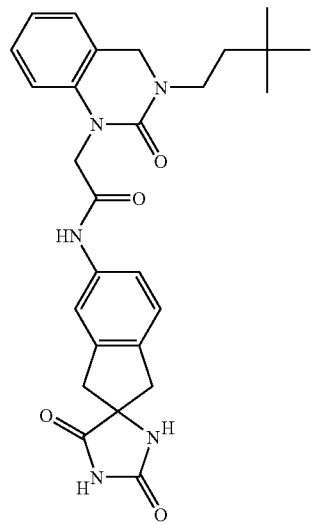
75
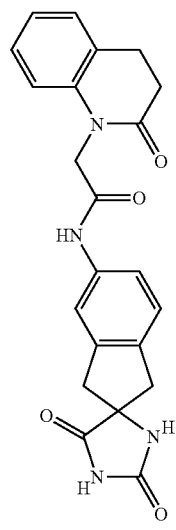
76
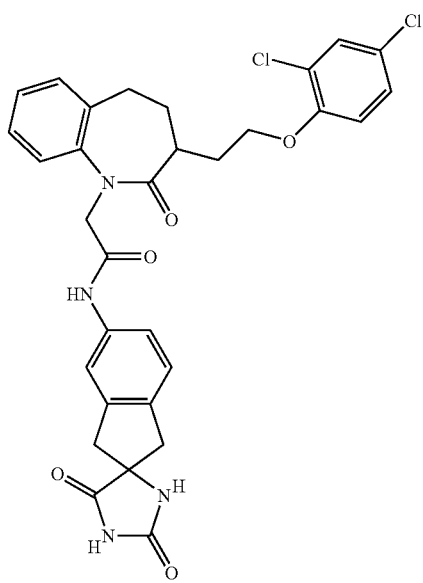

-continued

77

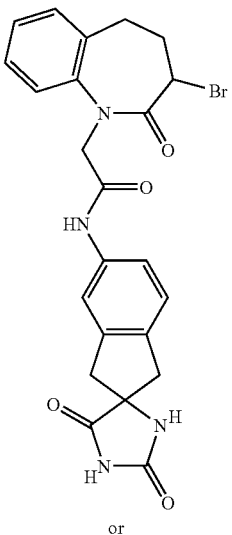

or

78

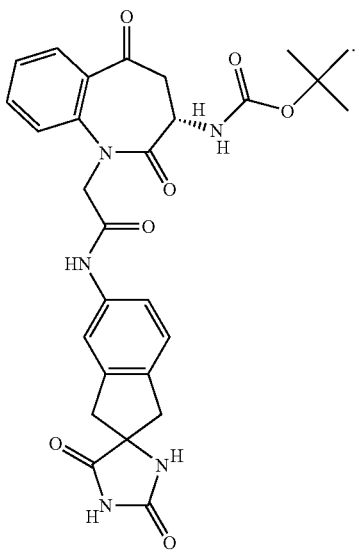

20. A pharmaceutical composition comprising a compound according to claim 1 or claim 19, and a pharmaceutically acceptable carrier, adjuvant, or vehicle.

21. A method for the treatment of a disease or disorder in a patient, wherein said disease or disorder is selected from headache or pain comprising administering to the patient a therapeutically effective amount of a composition according to claim 20.

22. The method according to claim 21, wherein said disease or disorder is selected from pain and said method is useful for the treatment of chronic pain; neurogenic inflammatory pain; neuropathic pain; eye pain and tooth pain.

23. The method according to claim 21, wherein said disease or disorder is selected from headache and said method is useful for the treatment of migraine; cluster headache and chronic tension type headache.

* * * * *